United States Patent
Freeman et al.

(10) Patent No.: US 10,349,875 B2
(45) Date of Patent: Jul. 16, 2019

(54) NON-INVASIVE ASSESSMENT OF PHYSIOLOGICAL PARAMETERS OF TISSUE VIA NEAR INFRARED SPECTROSCOPY TO DISTINGUISH BETWEEN ARRHYTHMIC AND ASPHYXIAL ARREST

(71) Applicant: ZOLL Medical Corporation, Chelmsford, MA (US)

(72) Inventors: Gary A. Freeman, Waltham, MA (US); Ulrich Herken, Medford, MA (US); Christopher L. Kaufman, Somerville, MA (US); Annemarie Elizabeth Silver, Bedford, MA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 285 days.

(21) Appl. No.: 15/281,363

(22) Filed: Sep. 30, 2016

(65) Prior Publication Data

US 2017/0086719 A1 Mar. 30, 2017

Related U.S. Application Data

(60) Provisional application No. 62/235,228, filed on Sep. 30, 2015.

(51) Int. Cl.
*A61B 5/145* (2006.01)
*A61B 5/1455* (2006.01)

(52) U.S. Cl.
CPC ...... *A61B 5/14539* (2013.01); *A61B 5/14551* (2013.01)

(58) Field of Classification Search
CPC .. G06F 19/00; A61B 5/14539; A61B 5/14551
See application file for complete search history.

(56) References Cited

U.S. PATENT DOCUMENTS

| 2011/0205535 | A1 | 8/2011 | Soller et al. |
| 2014/0296675 | A1* | 10/2014 | Freeman ............... A61B 5/7264 |
| | | | 600/361 |

OTHER PUBLICATIONS

Bai, "Noninvasive near infrared spectroscopy on living tissue with multivariate calibration approaches," Dissertation, University of Iowa, Fall 2010, available at http://ir.uiowa.edu/etd/776, (208 pages).
Bobrow, et al., "Minimally Interrupted Cardiac Resuscitation by Emergency Medical Services for Out-of-Hospital Cardiac Arrest," JAMA, vol. 299, No. 10, pp. 1158-1165, Mar. 12, 2008 (8 pages).
Corbett, et al., "Effect of Hypoxia on Glucose-Modulated Cerebral Lactic Acidosis, Agonal Glycolytic Rates, and Energy Utilization," Pediatric Research, 39, 1996, pp. 477-486 (16 pages).
Weisfeldt, et al., "Resuscitation After Cardiac Arrest A 3-Phase Time Sensitive Model," JAMA, vol. 288, No. 23, Dec. 18, 2002, pp. 3035-3038, (4 pages).

* cited by examiner

*Primary Examiner* — Christine H Matthews
*Assistant Examiner* — Joshua Daryl D Lannu
(74) *Attorney, Agent, or Firm* — Wilmer Cutler Pickering Hale and Dorr LLP

(57) ABSTRACT

Near-infrared spectroscopy (NIRS) is used to measure parameters such as pH of muscle tissue of a patient that is affected by a cardiac arrest. Analysis of the pH and other parameters such as $SmO_2$ facilitates distinguishing between an arrhythmia arrest and an asphyxia arrest.

41 Claims, 18 Drawing Sheets

Figure V-1. Comparison of glucose, lactate, and urea absorptivities in the combination region.

NON-INVASIVE ASSESSMENT OF PHYSIOLOGICAL PARAMETERS OF TISSUE VIA NEAR INFRARED SPECTROSCOPY TO DISTINGUISH BETWEEN ARRHYTHMIC AND ASPHYXIAL ARREST

CROSS REFERENCE TO RELATED APPLICATIONS

This application claims priority to U.S. Provisional Application No. 62/235,228, filed on Sep. 30, 2015, which is incorporated by reference.

TECHNICAL FIELD

Embodiments of the present invention relate generally to using spectral sensors for measuring physiological parameters of tissue such as, for example, muscle oxygenation ($SmO_2$) and/or pH, and more specifically to using spectral measurements for identifying a type of cardiac arrest affecting a patient.

BACKGROUND

Ventricular fibrillation/arrhythmia and asphyxia account for a significant percentage of cardiac arrests. The course of a cardiac arrest, neurological deficit and myocardial dysfunction differs between these two causes of cardiac arrest. For example, asphyxia cardiac arrest is characterized by a progressive clinical decline in cardiac function initiated by hypoxemia, hypercarbia, acidosis, hypotension and subsequent cessation of cardiac activity. Cardiac mitochondrial damage may be greater and occur more quickly with asphyxia cardiac arrest as compared to arrhythmia arrest. It is clinically valuable to be able to ascertain the cause of cardiac arrest so that an appropriate clinical response may be employed. For example, in many cases, an arrhythmic arrest may be treated by shocking the patient with a defibrillator, whereas an asphyxia arrest may be treated by shocking the patient with a defibrillator and by utilizing a ventilator.

Particularizing the treatment protocol to the patient "down time" or cardiac arrest phase of the patient can improve outcomes. See, for example, "Minimally Interrupted Cardiac Resuscitation by Emergency Medical Services for Out-of-Hospital Cardiac Arrest," Bobrow, Bentley J., M.D., et al., Journal of the American Medical Association, vol. 299, no. 10, Mar. 12, 2008, pp. 1158-1165, which is incorporated by reference herein. Previously it has been suggested that ventilator support or active ventilation may be delayed for several minutes or more in cardiac resuscitation treatment protocol. However, contrary to this suggestion, for cardiac arrest caused by asphyxia, sooner and/or more active ventilation treatment may be beneficial.

Also, a three-phase time-sensitive model for resuscitation after cardiac arrest has been described in the literature to include the following: the electrical phase, the circulatory phase, and the metabolic phase. See, e.g., "Resuscitation After Cardiac Arrest," Weisfeldt, Myron L., M.D., et al., Journal of the American Medical Association, vol. 288, no. 23, Dec. 18, 2002, pp. 3035-3038, incorporated by reference herein. Different treatment protocols may be indicated for different phases of resuscitation, and the phases may be identified (or at least estimated) based on the duration of time from the onset of the cardiac arrest, referred to as "downtime." It would also be preferable to further distinguish between cardiac arrest caused by ventricular fibrillation/arrhythmia and asphyxia to determine the treatment protocol.

SUMMARY

A system for distinguishing between arrhythmic cardiac arrest and asphyxial cardiac arrest in a patient who is undergoing cardiac arrest according to embodiments of the present invention includes one or more spectral sensors, wherein the spectral sensors are configured for placement above the patient's muscle tissue, and a processor communicably coupled to the one or more spectral sensors, wherein the processor is configured to determine at least one of tissue pH, tissue lactate and tissue oxygenation based on input received from the one or more spectral sensors, and determine, based on the at least one of tissue pH, tissue lactate and tissue oxygenation, whether the cardiac arrest is of arrhythmic or asphyxial etiology.

A system for distinguishing between arrhythmic cardiac arrest and asphyxial cardiac arrest in a patient who is undergoing cardiac arrest according to embodiments of the present invention includes one or more spectral sensors, wherein the spectral sensors are configured for placement above the patient's muscle tissue, and a processor communicably coupled to the one or more spectral sensors, wherein the processor is configured to determine a pH value based on input received from the one or more spectral sensors, and determine, based on the pH value, whether the cardiac arrest is of arrhythmic or asphyxial etiology.

A spectral sensor assembly for measuring pH of a patient's muscle tissue at a plurality of depths, wherein the patient is undergoing cardiac arrest according to embodiments of the present invention includes one or more radiation sources, a spectral detector, wherein at least one of the one or more radiation sources are located on the spectral sensor, and a processor communicably coupled to the one or more radiation sources, wherein the processor is configured to determine a pH value of underlying muscle tissue, and identify, based on the pH value, a level of degeneration in the muscle tissue, wherein the level of degeneration may facilitate determining whether the patient is undergoing arrhythmia arrest or asphyxial arrest.

A system according to embodiments of the present invention includes a spectral sensor assembly configured to obtain a near-infrared spectroscopy (NIRS) measurement, the NIRS measurement comprising at least one of a muscle tissue oxygenation ($SmO_2$) measurement and a tissue pH measurement, and a processor configured to analyze the NIRS measurement to identify a type of cardiac arrest affecting the patient.

A system for distinguishing between arrhythmic cardiac arrest and asphyxial cardiac arrest in a patient who is undergoing cardiac arrest according to embodiments of the present invention includes a spectral sensor, wherein the spectral sensor comprises one or more radiation sources and at least one spectral detector, wherein the spectral sensor is configured to obtain measurements associated with a patient tissue using a radiation spectrum, wherein at least a portion of the radiation spectrum is between a predetermined range, and a processor communicably coupled to the spectral sensor, wherein the processor is configured to determine tissue measurements for at least two points in time, the tissue measurements comprising at least one of a tissue lactate measurement and a tissue pH measurement, and determine, based on the tissue measurements, a downtime associated with the cardiac arrest.

A system for distinguishing between arrhythmic cardiac arrest and asphyxia cardiac arrest in a patient who is undergoing cardiac arrest according to embodiments of the present invention includes a spectral sensor, wherein the spectral sensor comprises one or more radiation sources and at least one spectral detector, wherein the spectral sensor is configured to obtain measurements associated with a patient tissue using a radiation spectrum, wherein at least a portion of the radiation spectrum is between a predetermined range, and wherein the spectral sensor is configured to be disposed on the patient in a core location, the core location being selected to result in the spectral sensor obtaining measurements from tissue perfused primarily by core blood vessels, and a processor communicably coupled to the spectral sensor, wherein the processor is configured to determine an estimated tissue oxygenation measurement, determine, based on the estimated tissue oxygenation, the cardiac arrest should be treatable as a cardiac arrest of arrhythmic etiology, and provide a prompt to the user based on the determination of whether the cardiac arrest should be treatable as a cardiac arrest of arrhythmic etiology.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
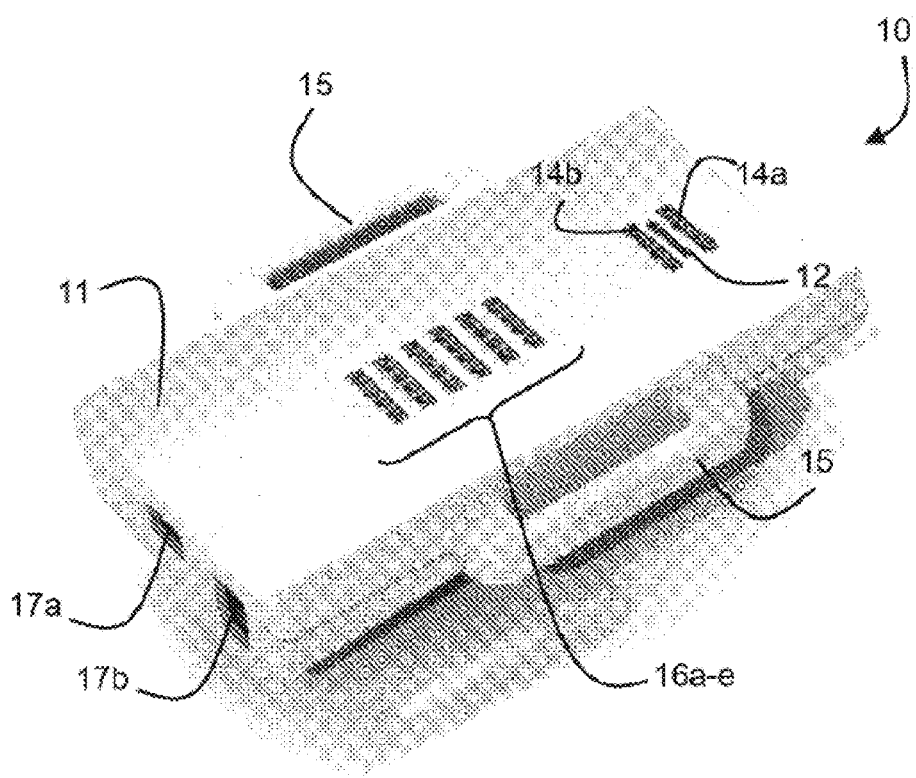
FIG. 1 illustrates a prior art spectral sensor.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Near-infrared spectroscopy (NIRS) technology may be used in conjunction with patient monitors to assess physiological parameters of tissue to help distinguish between arrhythmic and asphyxia arrest (e.g., to help in determining whether the cardiac arrest was of asphyxial or arrhythmic etiology). NIRS technology may include, for example, using a radiation spectrum, where at least a portion of the radiation spectrum is between 250 nm and 4500 nm.

Figure 2:
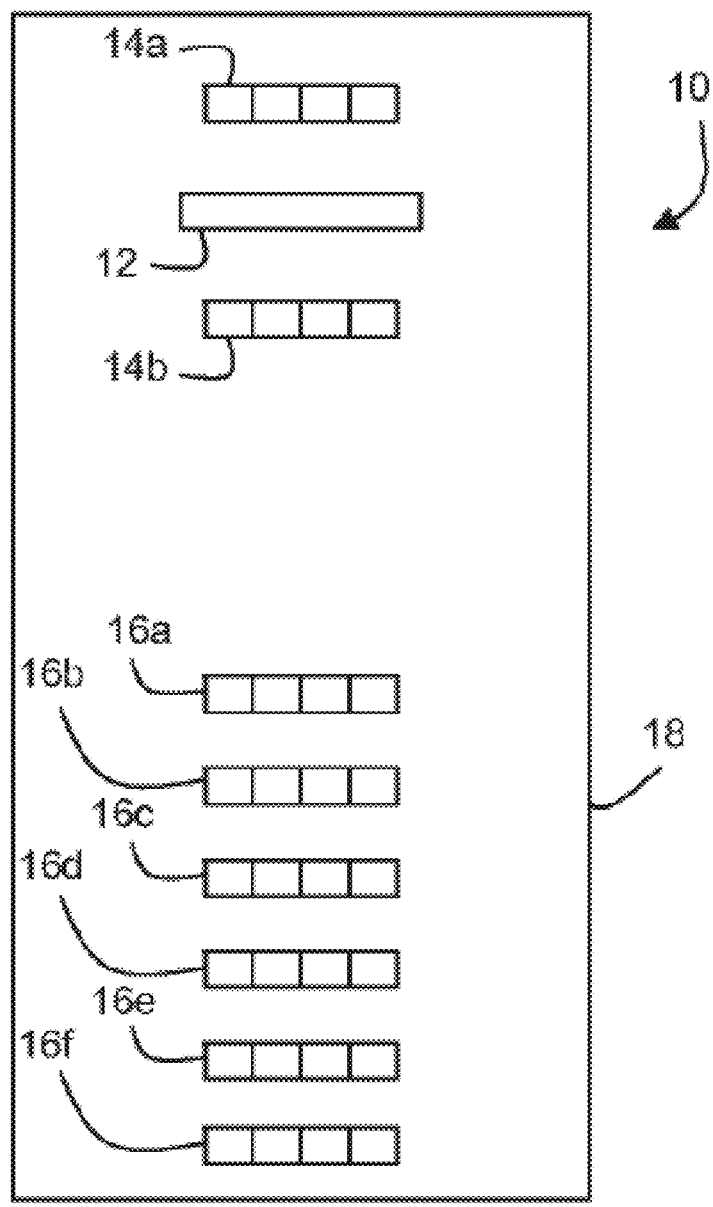
FIG. 2 illustrates a bottom schematic view of placement of radiation sources and a detector of the prior art spectral sensor of FIG. 1.

Spectral sensors for noninvasive measurement or calculation of oxygen saturation, oxygen tension, pH, hematocrit, hemoglobin concentration, anaerobic threshold, water content, and oxygen consumption are described in the art, for example in U.S. Patent Application Publication No. 2011/0205535, published Aug. 25, 2011 ("the '535 Publication"), the contents of which are incorporated by reference herein in their entirety for all purposes. One such spectral sensor 10 is illustrated in FIGS. 1 and 2, reproduced from the '535 Publication, which show a spectral detector 12, two short-distance radiation sources 14a, 14b, and six long-distance radiation sources 16a-16e. Spectral detector 12 may be configured to obtain measurements associated with a patient tissue using a radiation spectrum, wherein at least a portion of the radiation spectrum is between a predetermined range. In some embodiments, at least a portion of a radiation spectrum used to obtain measurements comprises visible light. Also in some embodiments, at least a portion of a radiation spectrum used to obtain measurements comprises ultraviolet (UV) light. The housing 11 includes a concave inner surface that is configured for placement against a patient's skin above tissue, for example peripheral muscle tissue, which is to be monitored. The housing 11 further includes a handle 15 on each side, as well as apertures 17a, 17b for communications interface. As shown in FIG. 2, the radiation sources 14a, 14b and 16a-16e may be part of a circuit board 18. Other spectral sensors may be employed, such as NIRS sensors that are configured to measure cerebral oxygenation. As further context, NIRS may be used to provide a continuous non-invasive measure of hemoglobin saturation and systemic oxygenation. NIRS may further be used in transcranial cerebral oximetry to measure regional cerebral oxygen saturation. NIRS is based on the principle of transmission and absorption of near infrared light (approximately 700-1000 nm) as it passes through tissue. The absorption of near infrared light is proportional to the concentration of iron in hemoglobin and copper in cytochrome aa3. Because oxygenated and deoxygenated hemoglobin have different absorption spectra, the oxygenation status can be determined. Cerebral oximeter probes can be placed anywhere on the head but most commonly on regions where there is the least amount of interference (e.g., from hair). Oximeter probes typically include a fiber optic light source and light detector(s), where the fiber optic strands release light amplification by stimulated emission of radiation or light emitting diodes light. The emitted light wavelengths are sent from the light source penetrating the skull and cerebrum, and the light detector(s) receives the light not absorbed during the light pathway through the skull and cerebrum. The amount of oxygen present in the brain can be determined from the difference between the amount of light sent and received by the probe, which is often suggested by a percentage of oxygen provided to a user.

Figure 12:
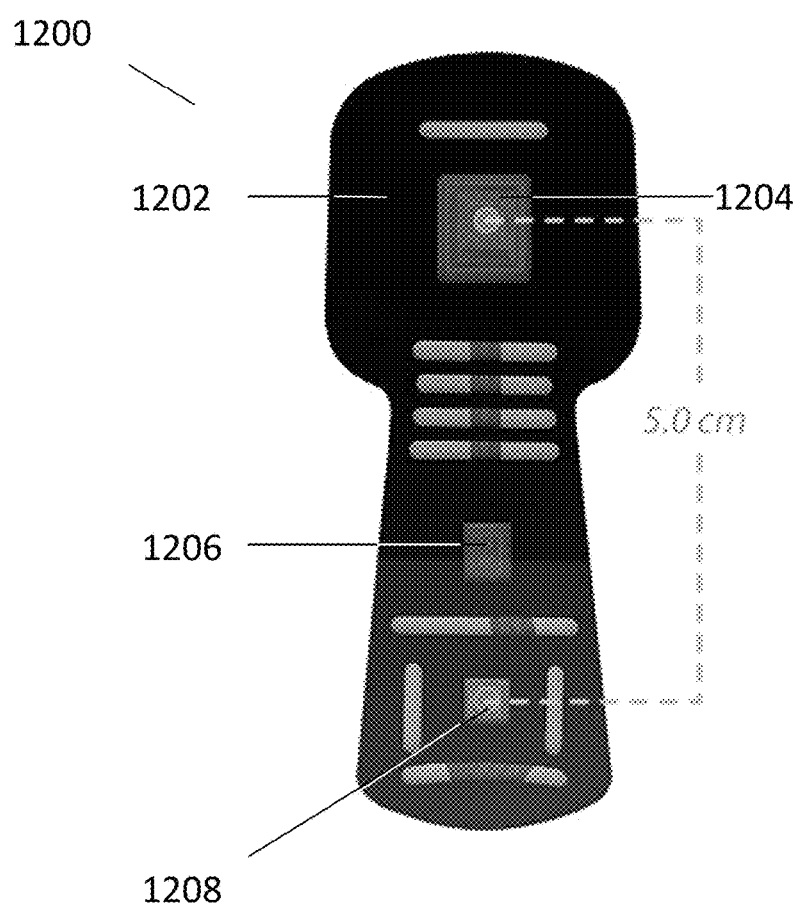
FIG. 12 illustrates a spectral sensor configured for placement on a patient's head, according to embodiments of the present invention.

FIG. 12 illustrates another such type of spectral sensor 1200 which, according to some embodiments, can be configured to obtain measurements associated with a patient's cerebral tissue. Spectral sensor 1200 can comprise a body 1202, at least one radiation source 1204, and at least one spectral detector, such as spectral detectors 1206 and 1208. The radiation source 1204 can emit radiation similar to radiation sources 14a, 14b, and 16a-16e in FIG. 2. In some embodiments, the radiation emitted by radiation source 1204 can have the same wavelength, or set of wavelengths, as radiation emitted by radiation sources 14a, 14b, and/or 16a-16e. In other embodiments, the radiation emitted by radiation source 1204 can have different wavelengths, or a different set of wavelengths. Radiation source 1204 can be configured to direct radiation through a skull, skin layer, or adipose tissue layer of a patient, so as to illuminate the patient's cerebral (e.g., brain) tissue. Similar to spectral detector 12 in FIG. 2, spectral detectors 1206 and 1208 can detect radiation reflected from the patient's tissue. As shown, spectral detectors 1206 and 1208 may be positioned 5.0 cm apart on body 1202, but shorter or longer distances are also possible. Examples of spectral sensors 1200 include spectral sensors manufactured by Nonin Medical Inc. in Plymouth, Minn., and CAS Medical Systems, Inc. (CASMED) in Branford, Conn.

Figure 13A:
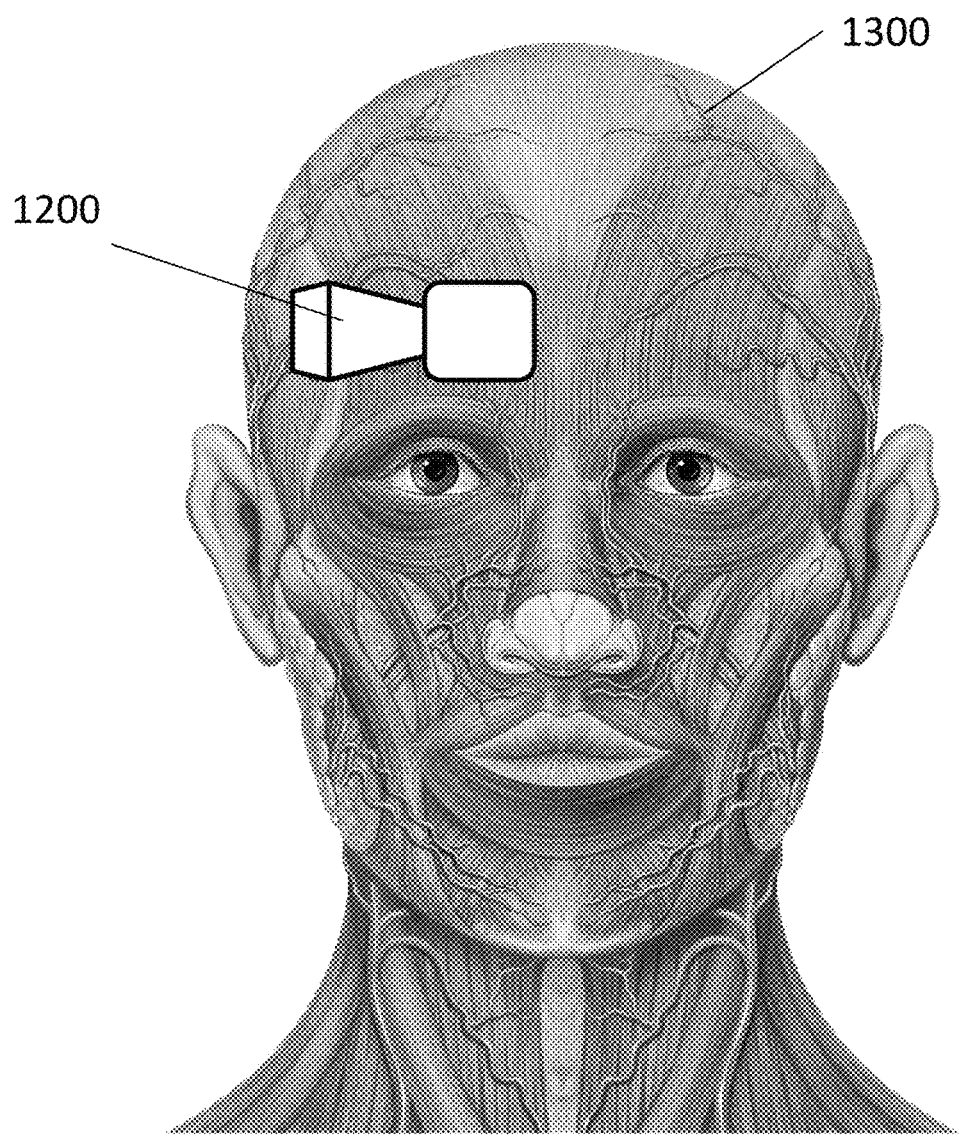
FIGS. 13A and 13B illustrate possible placements of one or more spectral sensors on a patient's head, according to embodiments of the present invention.
Figure 13B:
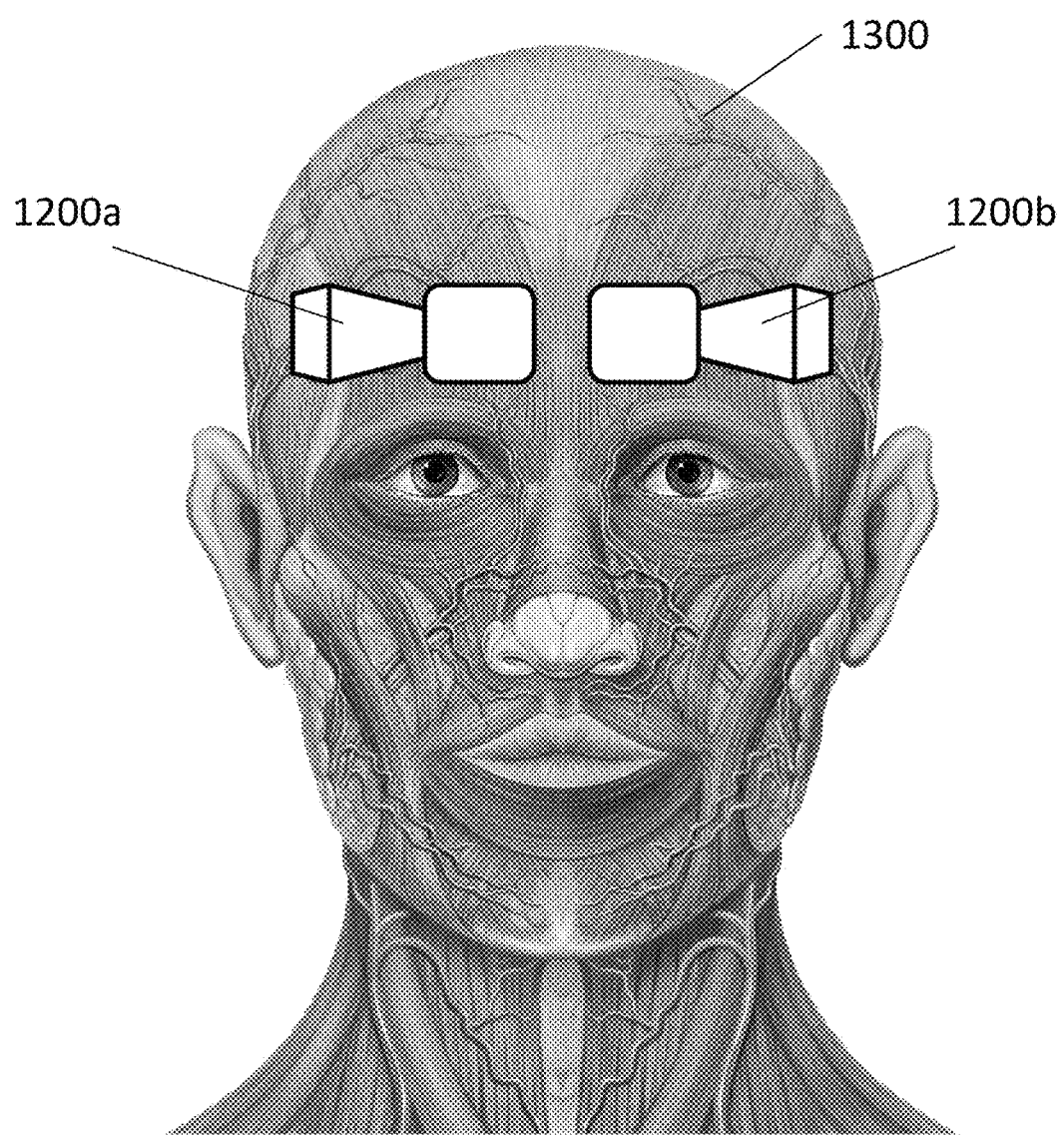
Figure 14:
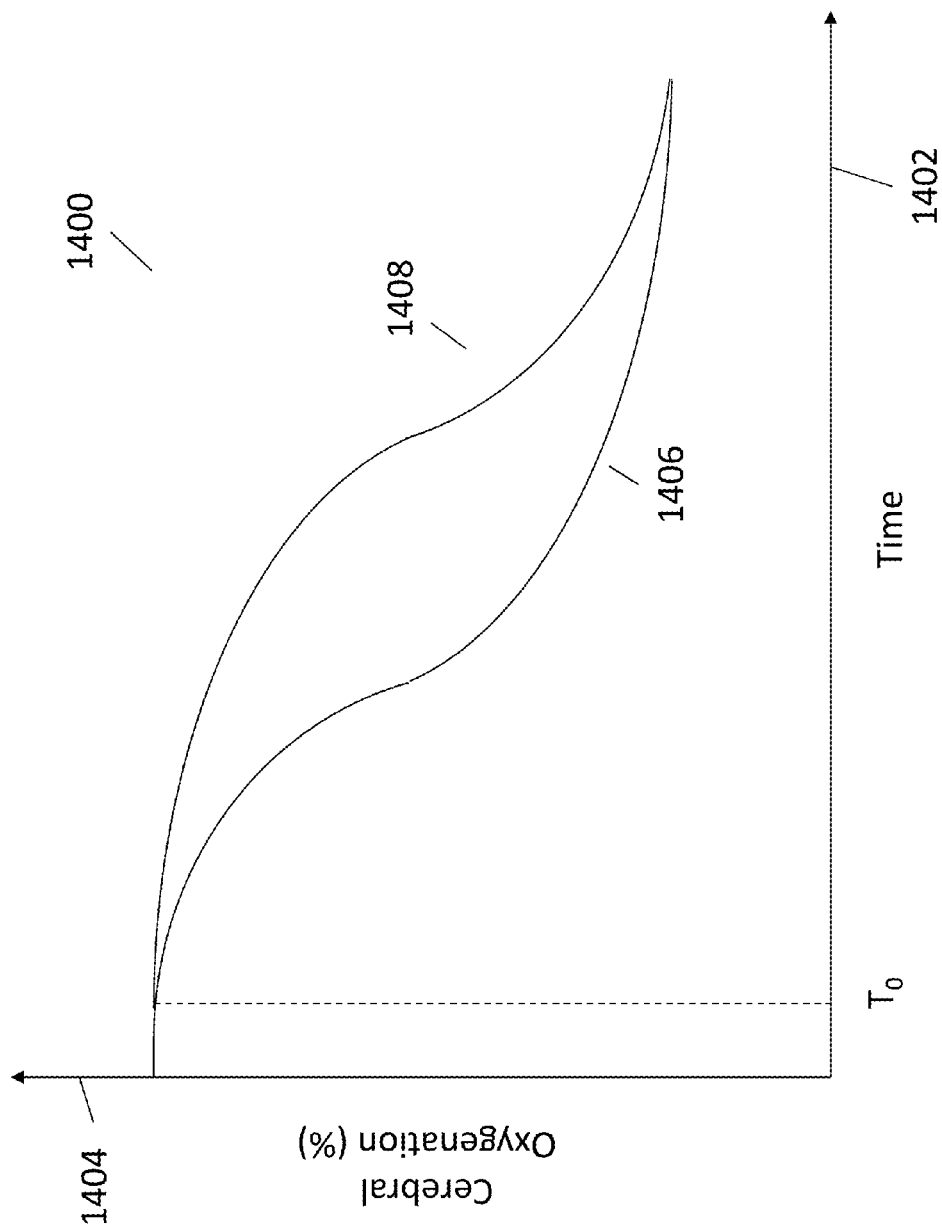
FIG. 14 depicts a conceptual plot of a patient's cerebral oxygenation levels versus time in an arrhythmic cardiac arrest and an asphyxia cardiac arrest.

FIGS. 13A and 13B show possible placements of spectral sensor 1200 on a head 1300 of a patient. As depicted in FIG. 13A, a single spectral sensor 1200 may be placed on one side of the patient's forehead. In other embodiments, as illustrated in FIG. 13B, two or more spectral sensors 1200a and 1200b may be used, one on each side of the patient's forehead. Other ways to place cerebral spectral sensors are also possible. For example, in some cases, spectral sensors may be shaped as a thin wand (not shown), and inserted into the patient's nasal passage. Such wand-shaped spectral sensors may be particularly useful for illuminating the base of the patient's brain, such as the hippocampus region.

Figure 3:
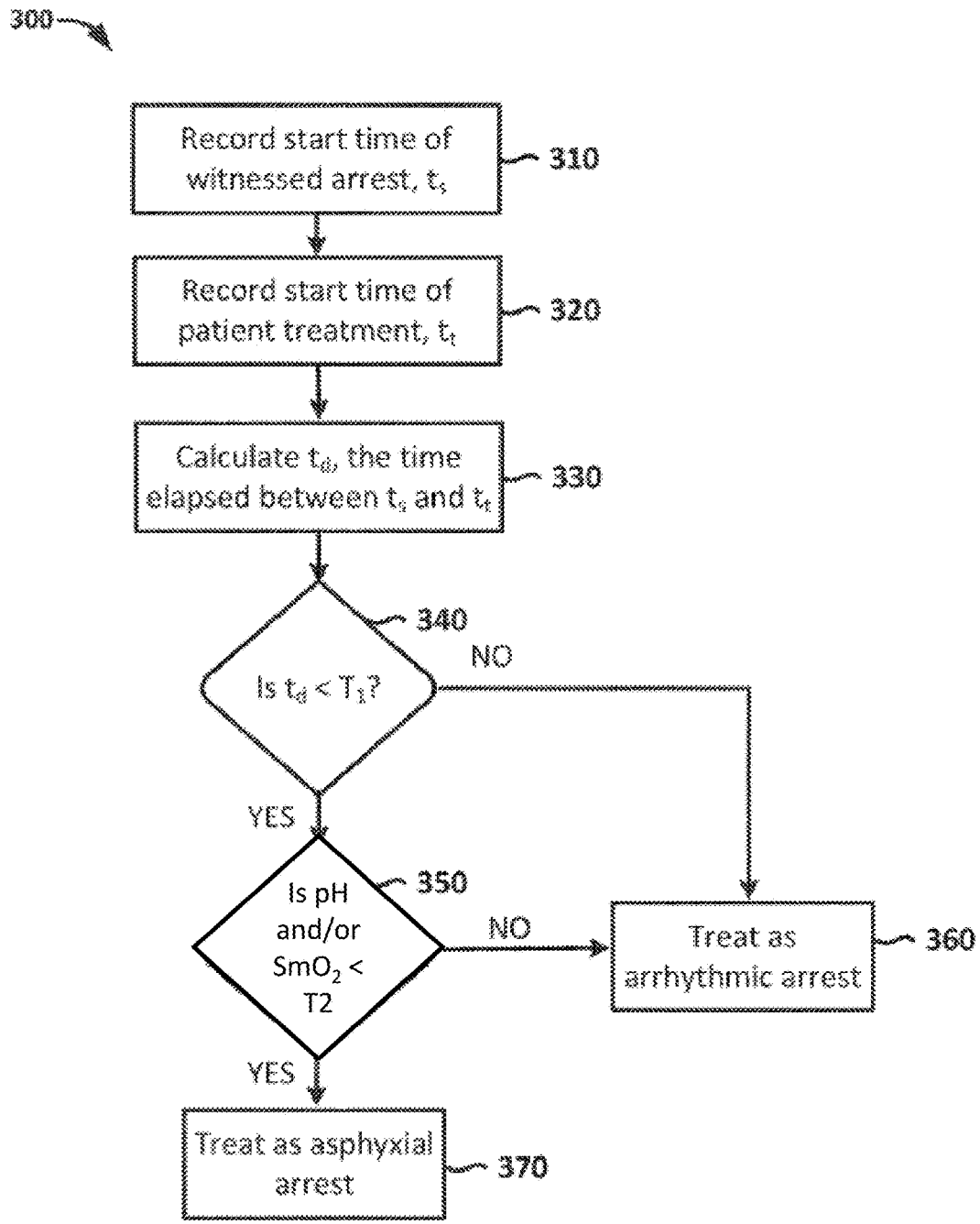
FIG. 3 illustrates a flow chart depicting an illustrative method for determining patient down time and combining the patient down time with tissue pH and/or oxygen saturation, according to embodiments of the present invention.

In embodiments, tissue pH and/or tissue oxygen saturation (e.g., muscle oxygen saturation, $SmO_2$) may be utilized such as that estimated using an NIR probe having a spectral sensor, e.g., the Reflectance Medical NIR probe (Westborough Mass.), or spectral sensors 1200 depicted in FIG. 12 (Nonin Medical Inc., Plymouth Minn., or CAS Medical Systems, Inc. (CASMED) (Branford Conn.). In certain embodiments the tissue pH and/or oxygen saturation may be utilized in combination with other information to determine whether the cardiac arrest was of asphyxial or arrhythmic etiology. As one example, the patient down time can be determined and combined with tissue pH and/or oxygen saturation, as illustrated by the exemplary method 300 shown in FIG. 3. Where the time of arrest is known, e.g. in the case of a witnessed arrest, or where it can otherwise be calculated or estimated, this information can be combined with the tissue pH and/or oxygen saturation to determine the cause of the arrest and subsequent treatment. In Step 310 a rescuer records the time of cardiac arrest ($t_s$), e.g. by starting a timer, entering the time in a computing device, etc. In Step 320 the rescuer (or a monitoring device, treatment device, etc.) records a treatment start time, $t_t$ (e.g. time at which a spectral sensor starts measuring tissue pH and/or muscle saturation). At Step 330, the time elapsed between the treatment start time ($t_t$) and time of cardiac arrest ($t_s$), which may be termed patient downtime, $t_d$, is obtained. In Step 340, if $t_d$ is not less than a predetermined threshold, T1 (which may be, e.g., under about 12 minutes), it is indicated that the patient should be treated as usual for arrhythmic arrest as shown by Step 360. Step 340 can be repeated periodically, either automatically or manually upon user request. However, if $t_d$ is less than T1, tissue pH and/or oxygen saturation is compared to a second threshold, T2, in Step 350. In one example, if the pH is less than a threshold, T2, of 7.0, then the processor 116 determines that the patient should be treated as one suffering from asphyxia arrest as shown by Step 370 (as it is likely that a patient who has low tissue pH and/or oxygen saturation soon after cardiac arrest suffered from hypoxia induced arrest). Alternatively, the tissue oxygenation, $S_mO_2$, threshold may be 35.

In an alternate embodiment, the threshold, T2, may be a function of estimated downtime, $t_d$. For instance, the function used may be a simple linear one:

$$T2_{pH} = -0.033 * t_d + 7.2,$$

Whereby the tissue pH threshold is 7.2 at $t_d=0$, and 6.8 at a time of 12 minutes. The function may also be defined based on use of such techniques as linear regression by statistical analysis form a clinical database where the etiology, tissue pH and downtime is known. Alternatively, the function may also be non-linear.

In additional embodiments, at least two probes (e.g., spectral sensors) may be attached to the patient to estimate $SmO_2$ values for tissue at two or more locations, for example, the first location measuring $SmO_2$ substantially at the periphery ($S_mO_{2P}$), such as a shoulder, arm or leg; and at least a second location measuring tissue supplied by blood vessels that are relatively more associated with the patient's core ($S_mO_{2C}$) than the first location, such as the head (e.g., cerebral tissue), tongue or trapezius muscle (or other upper back muscle).

The tongue may be particularly good at representing core circulation (e.g. as measured by $S_mO_{2C}$) as it receives its blood supply primarily from the lingual artery, a branch of the external carotid artery. The lingual veins drain into the internal jugular vein. The floor of the mouth also receives its blood supply from the lingual artery. There is also a secondary blood supply to the tongue from the tonsillar branch of the facial artery and the ascending pharyngeal artery. Prior to the delivery of a vasopressor like epinephrine, the deviation between $S_mO_{2C}$ and $S_mO_{2P}$ may be indicative of the duration of arrest. The head may also be a good location for assessing core circulation.

When the patient is first assessed by the clinician or other rescuer, it must first be determined whether the patient is in cardiac arrest. The patient is considered to be in cardiac arrest if they are assessed to be: 1) not moving; 2) non-responsive; 3) not breathing; and 4) no palpable pulse. These can be assessed without need for any monitoring equipment, though a pulse oximeter or end tidal $CO_2$ monitor may be of assistance in improving the accuracy of the manual assessment by the clinician. However, clinicians are generally unable, using manual assessment or conventionally-available technology, to reliably distinguish between cardiac arrest of asphyxia or arrhythmic etiology.

A simple form of embodiments of the system may be implemented using one sensor located on the head, tongue or other core circulation tissue. If $S_mO_{2C}$ is low (e.g. less than 35), then a determination may be made that the arrest is either due to arrhythmia or downtime is very long; in either case, the patient may be treated as though the patient is in arrest due to arrhythmic etiology. For example, the system may prompt the rescuer by such common means as text on a display, voice or audio prompts, or pictorial diagrams displayed on a display of a measuring device or on a separate display such as an iphone or ipad or other portable computing device connected to the measuring device via such known means as Bluetooth, WiFi, etc.

Figure 4:
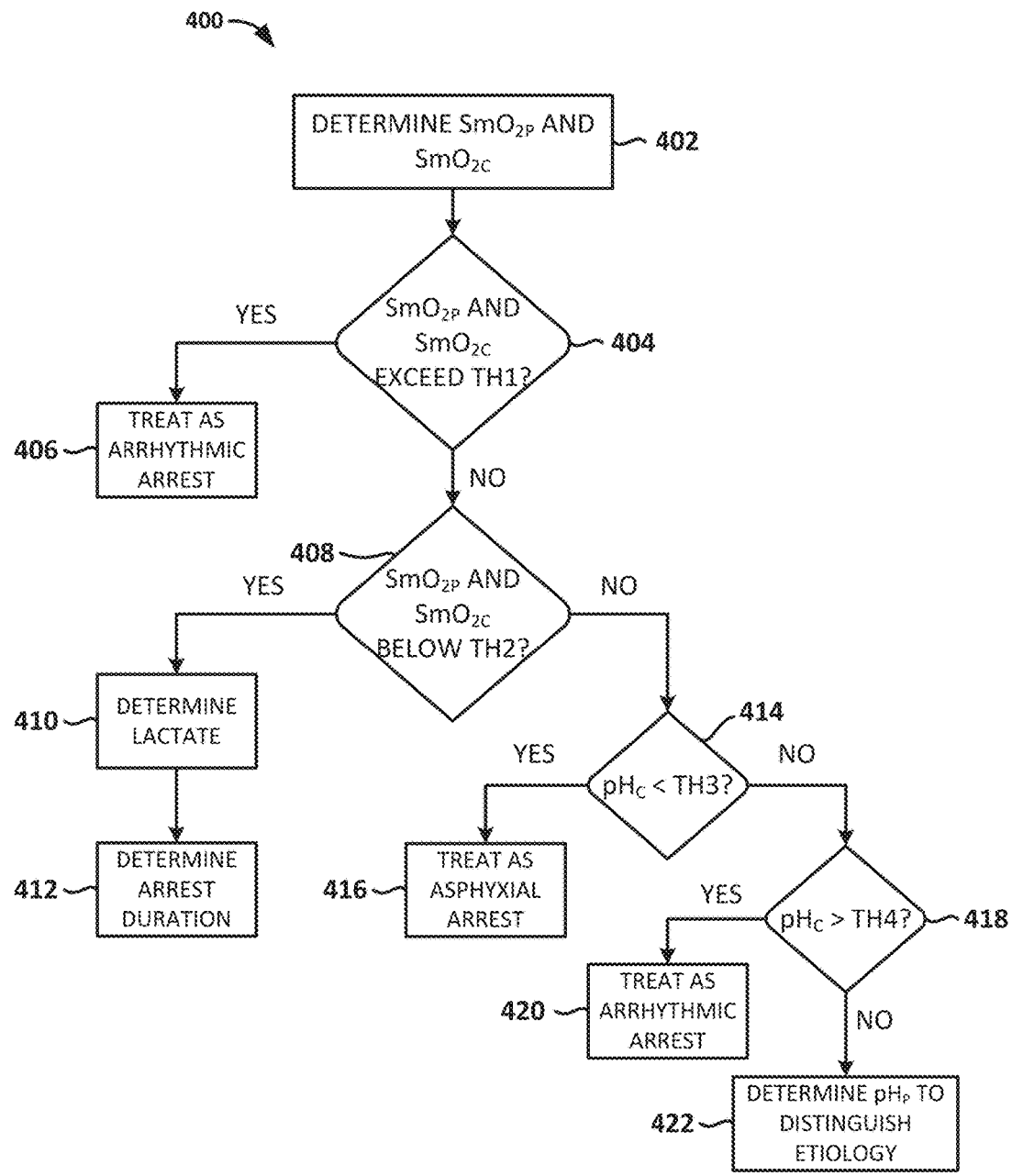
FIG. 4 is a flow chart depicting another illustrative method for determining a type of cardiac arrest affecting a patient, according to embodiments of the present invention.

An illustrative method 400 of the embodiments envisioned herein for determining a type of cardiac arrest affecting a patient is depicted in FIG. 4. After determination of cardiac arrest, in embodiments, NIR tissue probes (e.g., spectral sensors) are placed on a peripheral location (e.g., the forearm) and a core location (e.g., on the top surface of the tongue) and $S_mO_{2C}$ and $S_mO_{2P}$ measurements are determined (block 402). The peripheral and core tissue oxygenation measurements ($S_mO_{2C}$ and $S_mO_{2P}$) can be compared to thresholds to determine how to treat the cardiac arrest. For example, when both $S_mO_{2C}$ and $S_mO_{2P}$ are high (e.g., greater than a threshold ("TH1"), which may be, e.g., about 45—e.g., within 10 units of 45) (block 404), then the downtime is very short, and the patient should be treated as though they were in arrest due to arrhythmic etiology (block 406), as it is unlikely that a hypoxic condition can result in a full cardiac arrest after a short patient down time.

If, on the other hand, both $S_mO_{2C}$ and $S_mO_{2P}$ are both low (e.g. less than a threshold, ("TH2") which may be, e.g., about 35—that is, e.g., within 10 units of 35) (block 408), then the duration of cardiac arrest is likely long (i.e. the metabolic phase), in which case the treatment may be the same for both etiologies. A third parameter, such as tissue lactate and/or any other parameter indicative of hypoxia, acidosis and/or lactic acidosis, may be determined (block 410) to further distinguish between asphyxia and arrhythmic etiologies for long downtime arrest (block 412). Tissue lactate may be measured via NIR spectroscopy, such as, for example, is described in the PhD thesis "Noninvasive near infrared spectroscopy on living tissue with multi-variate calibration approaches", Chuannan Bai, University of Iowa, Iowa Research Online, 2010 (see, e.g., FIG. 5), which is hereby incorporated herein in its entirety for all purposes. In embodiments, at least two measurements are taken of tissue lactate and/or tissue pH at approximately 15-120 second intervals and a measurement of the change in lactate is calculated. The change can be a slope such as with a linear estimate. It can be an interpolation, such as a spline of any polynomial order, and/or it can be a regression estimate of an exponential or other function.

Figure 5:
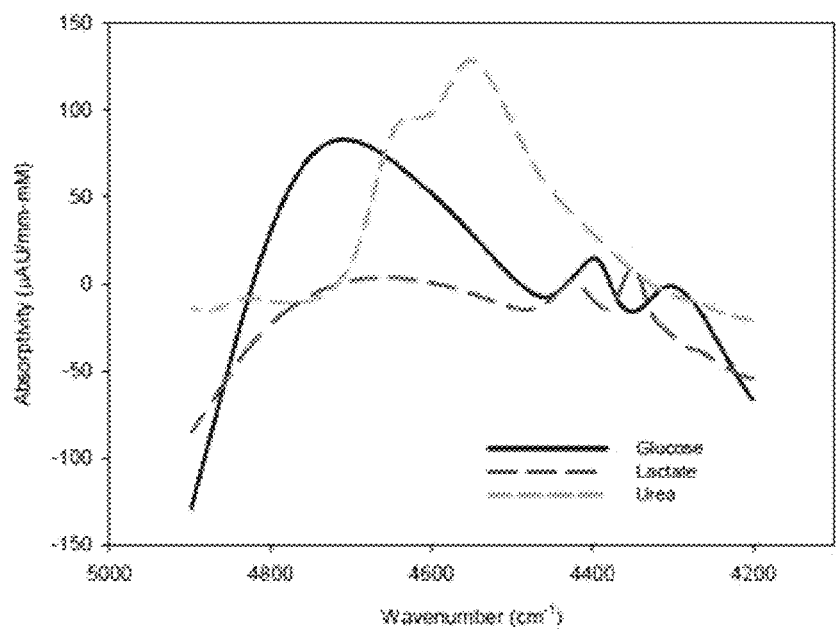
FIG. 5 is a graph of the prior art illustrating a comparison of glucose, lactate, and urea absorptivities in the combination region.
Figure 11:
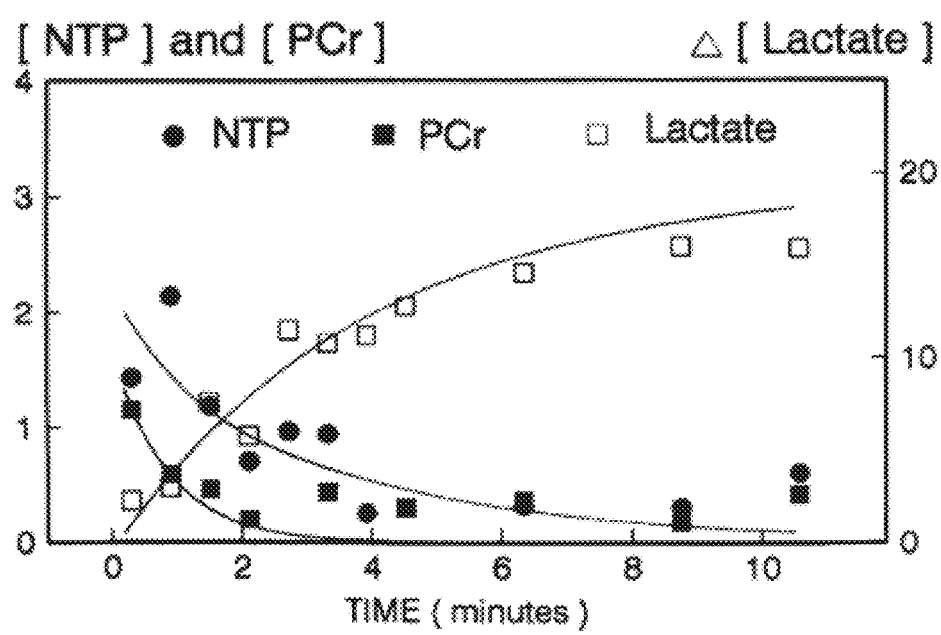
FIG. 11 is a graph of the prior art illustrating characteristics of lactate measurements in a metabolic phase.

Based on the estimated slope of the change and the absolute value of the measured tissue lactate level, the duration in the metabolic phase can be determined since the curve is generally shaped as an exponential, and determining the slope of the natural log of the lactate measurements determines the time constant of the exponential, as shown in FIG. 5, which is published in Corbett, Ronald J. T., et. al., "Effect of Hypoxia on Glucose-Modulated Cerebral Lactic Acidosis, Agonal Glycolytic Rates, and Energy Utilization," Pediatric Research (1996) 39, 477-486; doi:10.1203/00006450-199603000-00016, available at http://www.nature.com/pr/journal/v39/n3/full/pr1996104a.html, which is hereby incorporated by reference herein in its entirety for all purposes. In addition, separate slopes may be calculated for the periods of time before and after the start of chest compressions, as an initiation of chest compressions may result in a bolus of lactate being flushed from hypercarbic, venous-infused tissues. FIG. 11 is a graph of the prior art illustrating characteristics of lactate measurements in a metabolic phase.

Where $S_mO_{2C}$ is high (e.g. greater than 45) and $S_mO_{2P}$ is low (e.g. less than 35), it may indicate that the patient is in the circulatory phase of the cardiac arrest, as defined by Weisfeldt. In embodiments, if it has been determined that the patient is in the circulatory phase via the $SmO_2$ measure, then a tissue pH measure is determined. Note that "Tissue pH" and "muscle pH" are used interchangeably herein. In embodiments, the tissue pH may be determined using one or more spectral sensors disposed at a peripheral location, a core location, and/or both. For example, a tissue pH may be determined at a core site such as the head or the tongue (lingual site). In this case, if pH is low (e.g. less than a threshold ("TH3"), which may be about 6.9—that is, e.g., within 0.2 units of 6.9) (block 414) then the arrest is considered to be of asphyxial etiology (block 416); if, on the other hand, the pH is high (e.g., greater than a threshold ("TH4"), which may be about 7—that is, e.g., within 0.2 units of 7) (block 418), the arrest is considered to be of arrhythmic etiology (block 420). In embodiments, for example, a tissue pH may be determined at a head or a lingual core site and, if the tissue pH for the head or lingual core site ($pH_c$) is in an intermediate range of approximately 6.9 to 7.2, a pH measurement may be taken at a peripheral site ($pH_P$) to further distinguish between asphyxia and arrhythmic cardiac arrest (block 422). If $pH_C$ is greater than $pH_P$ by more than 0.2, then the arrest may be considered to be of asphyxial etiology.

In embodiments, for example, if a tissue pH obtained near a patient's core (e.g., by placing a NIRS sensor on a patient's head, or above an upper back muscle) indicates a low pH (e.g., about 6.8 or less), ventilation may be indicated, regardless of the cause of the cardiac arrest. If the core pH is in a high range (e.g., about 7.2—about 7.4), other asphyxia may not be indicated.

Instead of, or in addition to, using fixed thresholds to determine the type of etiology of cardiac arrest, an equation may be used with $S_mO_{2C}$, $S_mO_{2P}$, $pH_C$, and $pH_P$ to calculate an estimate of the probability that the arrest is of asphyxia etiology (the estimated probability for arrhythmic etiology is 1 minus the probability for asphyxia etiology since there are two choices). The equation may be the result of a logistic regression analysis, utilizing a training database of patient physiologic measures and known cardiac arrest etiologies in order to determine an optimal mathematical relationship between the four variables and the probabilities of the etiologies of cardiac arrest. The logistic may employ other variables as well, such as end tidal $CO_2$ ($EtCO_2$), retinal perfusion measures obtained through such known means as pupillometry such as the pupillometry system manufactured by NeurOptics (Irvine, Calif.). Pupillary Light Reflex (PLR)

may be a single parameter such as percent change or velocity or, as in the case of the Neuroptics, a composite measure of PLR.

The input variables may further be combined for various reason such as to scale, normalize and/or accentuate non-linear relationships. For example, the variables $S_mO_{2C}$, $S_mO_{2P}$ may be combined into a single variable to input the normalized difference:

$$(S_mO_{2C} - S_mO_{2P})/(S_mO_{2C} + S_mO_{2P})$$

Other methods for determination of arrest etiology may be based on known techniques such as fuzzy logic and neural networks, and/or in some cases neural networks supported by extreme learning machine techniques or support vector machine techniques.

In embodiments, NIRS sensors may be utilized to evaluate pH levels at various depths of muscle tissue to identify degeneration in metabolically active tissue which may also assist with identifying asphyxia arrest. In embodiments, for example, if a tissue pH obtained near a patient's core (e.g., by placing a NIRS sensor above an upper back muscle or the lingual location) indicates a low pH (e.g., about 6.8 or less), ventilation may be indicated, regardless of the cause of the cardiac arrest. If the core pH is in a high range (e.g., about 7.2-about 7.4), asphyxia may not be indicated.

According to embodiments, other combinations of physiological parameters may be evaluated to facilitate differentiating between arrhythmia arrest and asphyxia arrest. For example, tissue pH may be analyzed in conjunction with arterial oxygen saturation ($SpO_2$), $SmO_2$, ECG measurements, and/or the like. In some embodiments, a ratio of $SmO_2$ to tissue pH may be calculated, and the ratio may be used to differentiate between arrhythmia arrest and asphyxia arrest.

Figure 6:
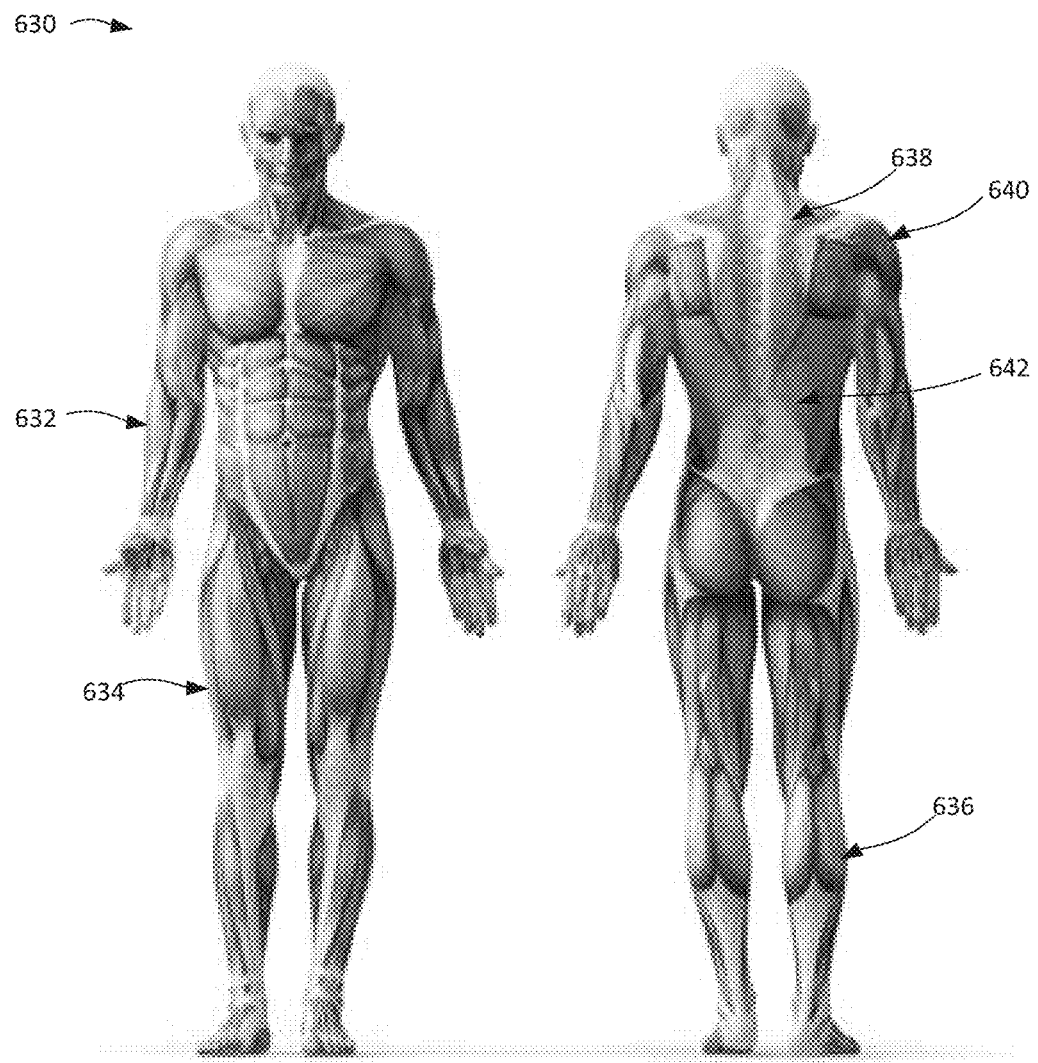
FIG. 6 illustrates a front and back view of a human body, illustrating the muscular system.
Figure 7:
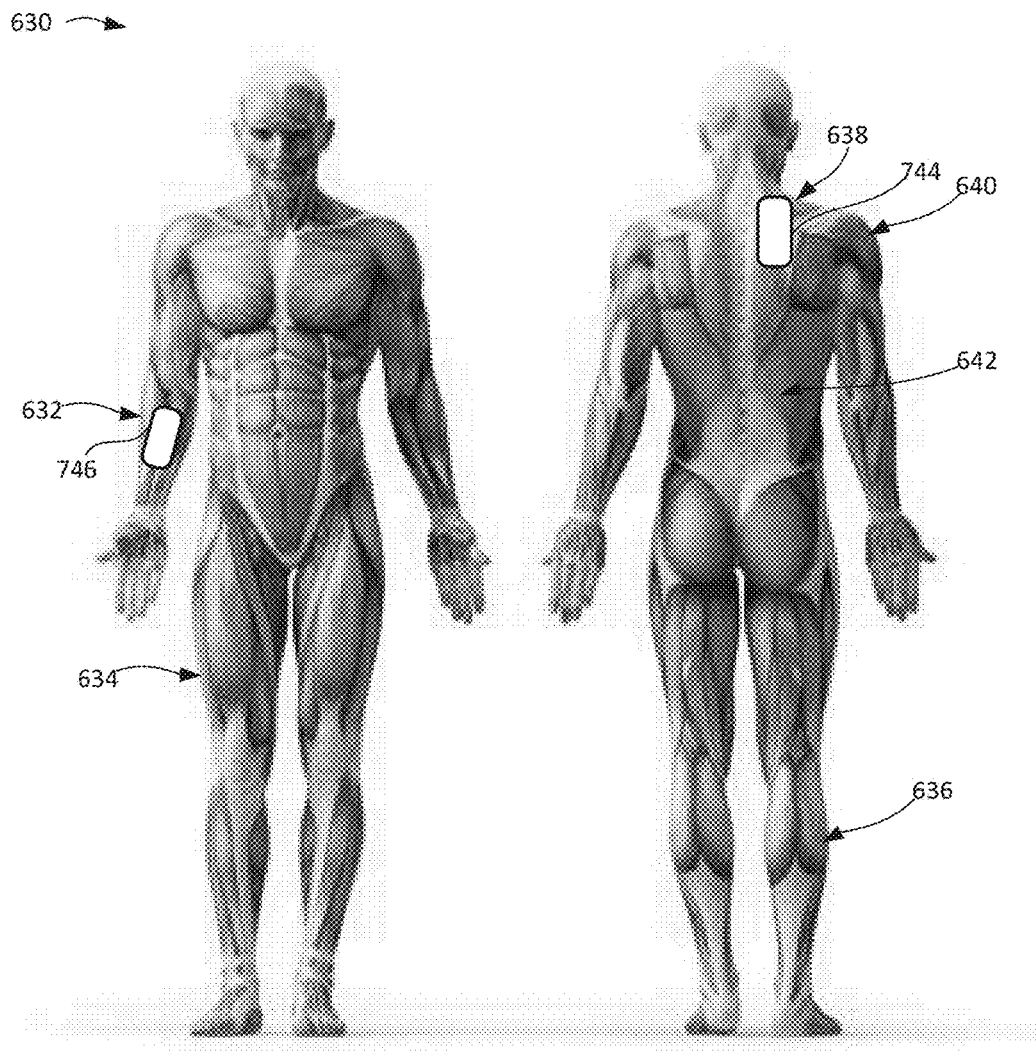
FIG. 7 illustrates placement of a pair of spectral sensors in the front and back view of FIG. 6, according to embodiments of the present invention.

FIG. 6 depicts front and back views of a human body 630, illustrating the muscular system. Muscle oxygen saturation ($SmO_2$) and tissue pH (pHm) may be measured using near-infrared spectroscopy (NIRS) at any number of different anatomical sites. Examples of such sites are depicted in FIG. 6. These include peripheral sites (e.g., the forearm 632, the thigh 634, and the calf 636) and sites that are near the patient's core (e.g., the trapezius 638, the deltoid 640, the latissimus dorsi 642, and/or the tongue). FIG. 7 illustrates placement of a first spectral sensor assembly 744 over the trapezius muscle (near the core of the patient) and a second spectral sensor assembly 746 over the forearm, according to embodiments of the present invention.

Figure 8:
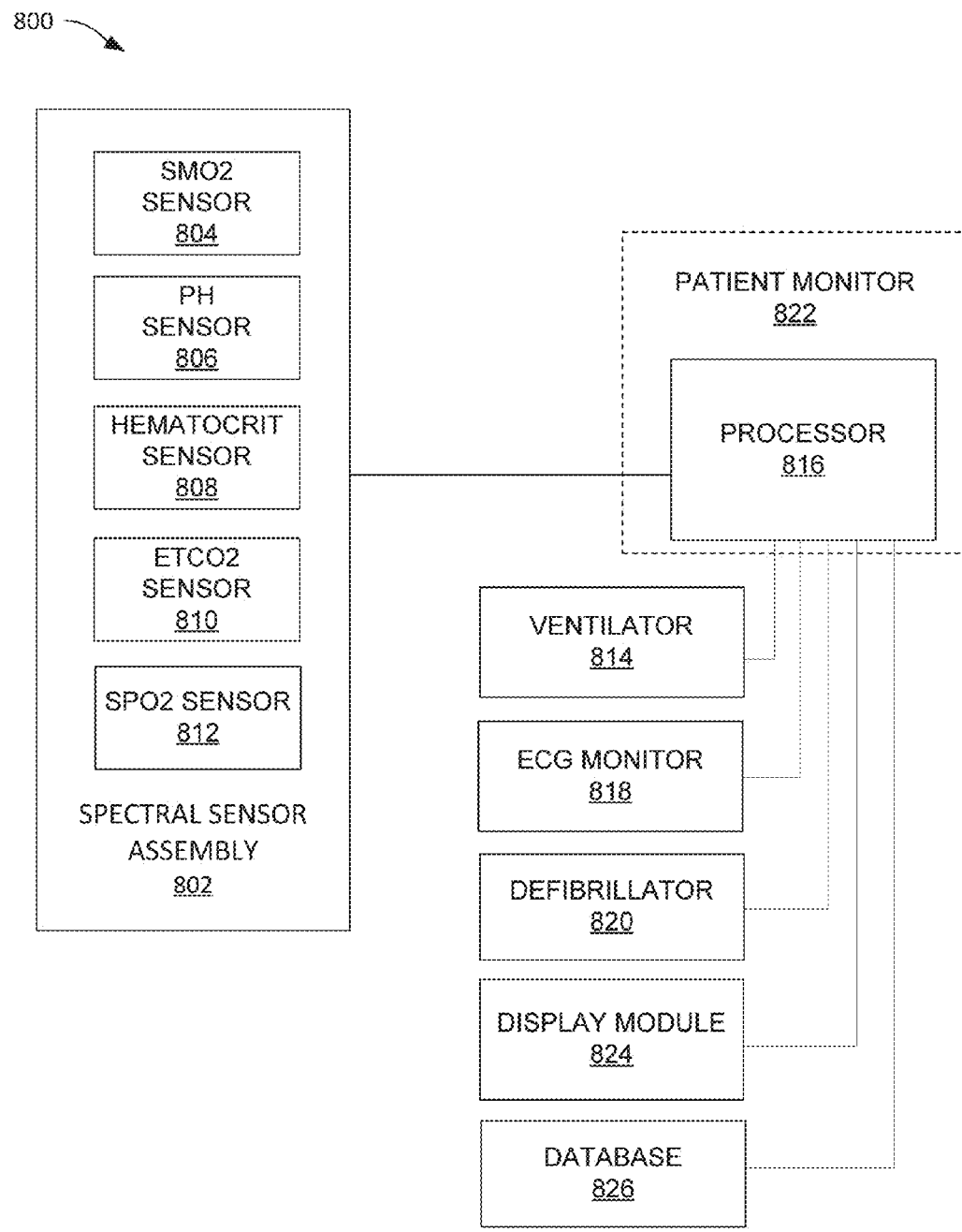
FIG. 8 illustrates a patient monitoring and control system including a spectral sensor, according to embodiments of the present invention.

FIG. 8 illustrates a patient monitoring and control system 800 including a spectral sensor assembly 802, according to embodiments of the present invention. The spectral sensor assembly 802 may include a muscle oxygen saturation ($SmO_2$) sensor 804, a pH sensor 806, a blood hematocrit sensor 808, an end-tidal carbon dioxide ($ETCO_2$) sensor 810, and/or a pulse oximetry sensor ($SpO_2$) 812 (referred to interchangeably herein as a "pulse oximeter"), according to embodiments of the present invention. In embodiments, the sensors 804, 806, 808, 810, 812 may each be part of the common spectral sensor assembly 802 that observes infrared spectroscopy characteristics of a patient's blood, to which the processor 816 may apply various algorithms to calculate and output $SmO_2$, pH, hematocrit values, $ETCO_2$, and/or $SpO_2$. In embodiments, any one or more of the sensors 804, 806, 808, 810, and 812 may be independent sensor devices.

For example, a spectral sensor assembly 802 may include one or more optical benches that houses spectral sensors capable of obtaining various types of measurements such as $SmO_2$ and/or pH, and the system 800 may include, for example, a separate pulse oximeter 812, and the $ETCO_2$ sensor 808 may be integrated with a ventilator 814. In embodiments, the one or more optical benches may include one or more long-distance radiation sources, one or more short-distance radiation sources, and one or more spectral detectors. The radiation sources may be located on the spectral sensor assembly at different distances from the spectral detector to facilitate obtaining measurements at various tissue depths. The one or more long-distance radiation sources, the one or more short-distance radiation sources, and the spectral detector are coupled to one or more optical benches disposed on a tissue-facing side of a sensor module (e.g., the spectral sensor assembly 802, or a housing thereof). In embodiments, the spectral sensor assembly 802 may be adapted to be applied to an extremity of a child. That is, for example, a sensor module may be about one inch wide, about three inches long, and about ¼ inch thick, or roughly about the same size and shape as a Band-Aid. Also in some embodiments, a first optical bench may comprise a sensor for obtaining an $SmO_2$ measurement, and a second optical bench may comprise a sensor for obtaining a pH measurement.

In embodiments, the sensors 804, 806, 808, 810, 812, and the ventilator 814 may communicate with a processor 816. The processor 816 may represent one or more processors 816 that may be disposed in one or more devices. For example, the processor 816, an ECG monitor 818, and a defibrillator 820 may all be integrated into a patient monitor 822 such as, for example, an X-Series Patient Monitor/Defibrillator, available from ZOLL® Medical. For example, the processor 816 may be communicably coupled to the one or more long-distance radiation sources and the one or more short-distance radiation sources and may be configured to determine a first pH, tissue lactate, and/or tissue oxygenation measurement of underlying muscle tissue at a first depth; determine a second pH, tissue lactate, and/or tissue oxygenation measurement of the underlying muscle tissue at a second depth; and identify, based on the first and second pH, tissue lactate, and/or tissue oxygenation measurements, a level of degeneration in the muscle tissue. In some embodiments, the identification of the level of degeneration in the muscle tissue based on the first and second measurements may comprise determining a difference between the first and second measurements. In embodiments, the level of degeneration may facilitate determining whether the patient is undergoing arrhythmia arrest or asphyxia arrest. In embodiments, other acute conditions may be detectable as well. For example, if a patient is experiencing asystole and has a very low pH, a clinician may be encouraged to determine whether that patient has a pulmonary embolism. In embodiments, the processor 816 may be communicably coupled to any number of spectral sensors and may be configured to perform various aspects of embodiments of the algorithms and analyses described herein such as, for example, those described with reference to FIGS. 4 and 10.

As indicated above, the patient monitor 822 may be, for example, a defibrillator or an automatic external defibrillator, according to embodiments of the present invention. The patient monitor 822 may include or otherwise be in communication with a processor 816, which is configured to or otherwise capable of executing all or parts of the methods described herein and/or described in the '535 Publication. The patient monitor 822 may have its own display module 824 in communication therewith, and/or the system 800 may include a separate display module 824, according to embodiments of the present invention.

Information about the physiological parameters as measured, or measured over time, by spectral sensor assembly 802 may be displayed on the display module 824 of the patient monitor 822 and/or the other display module 824, for example along with other data about a patient to which the spectral sensor assembly 802 is applied, according to embodiments of the present invention. Such data or information may also be stored in a database 826, for example, independently or with other information about the patient or the medical encounter for which the spectral sensor assembly 802 is being utilized. The hardware, software, and/or firmware elements and/or modules shown in FIG. 8 may be included on the same device and/or distributed across multiple devices, and each such hardware element or module shown in FIG. 8 may have its elements or functionality spread across multiple devices.

The illustrative system 800 shown in FIG. 8 is not intended to suggest any limitation as to the scope of use or functionality of embodiments of the present invention. Neither should it be interpreted as having any dependency or requirement related to any single component or combination of components illustrated therein. Additionally, any one or more of the components depicted in FIG. 8 may be, in embodiments, integrated with various ones of the other components depicted therein (and/or components not illustrated), all of which are considered to be within the ambit of the present invention.

Figure 9:
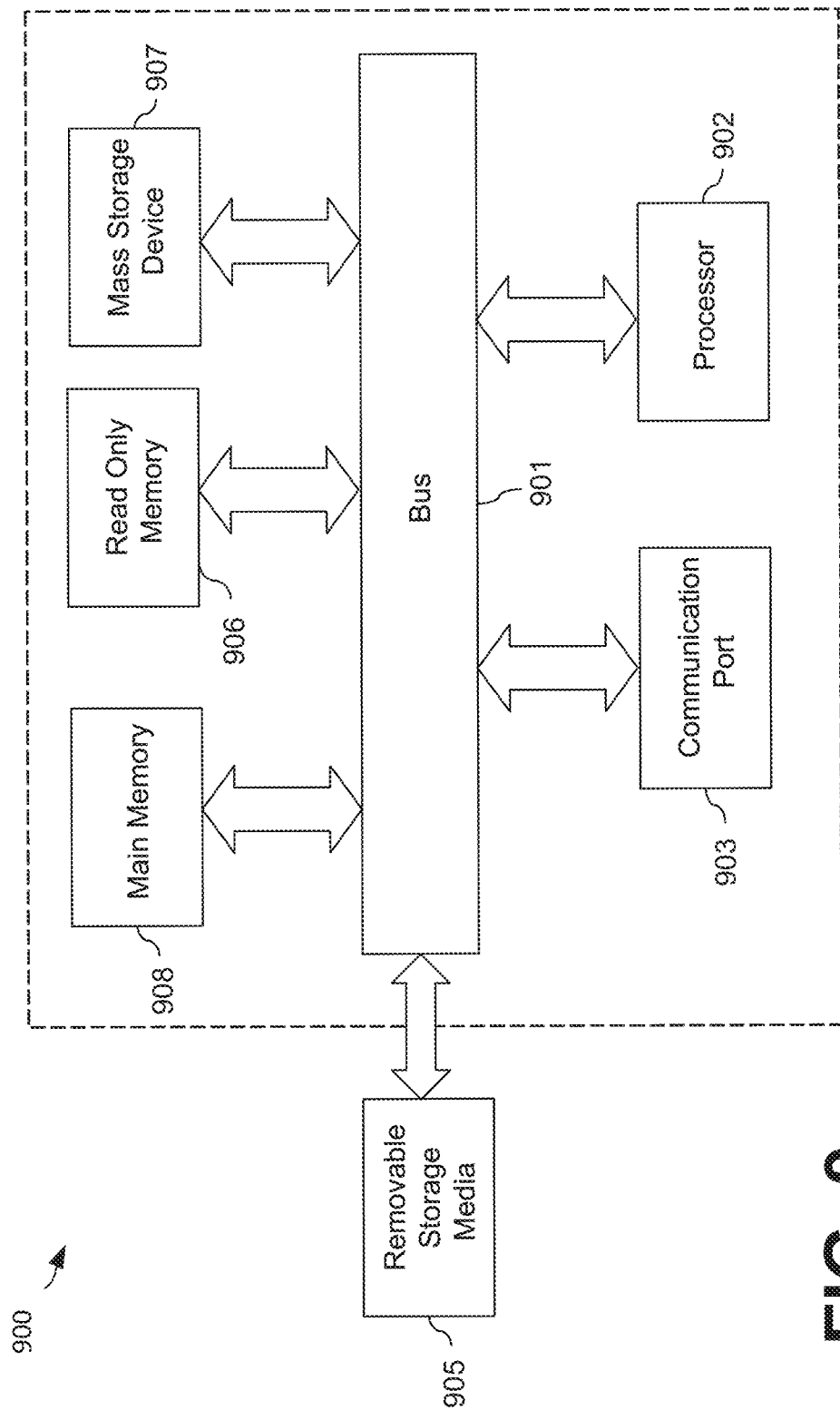
FIG. 9 illustrates a computer system, according to embodiments of the present invention.

FIG. 9 is an example of a computer or computing device system 900 with which embodiments of the present invention may be utilized. For example, any one or more of the components illustrated in FIG. 8 may be, incorporate, or be incorporated within, a computer system 900, according to embodiments of the present invention. According to the present example, the computer system includes a bus 901, at least one processor 902, at least one communication port 903, a main memory 908, a removable storage media 905, a read only memory 906, and a mass storage 907.

Processor(s) 902 can be any known processor, or any known microprocessor or processor for a mobile device. Communication port(s) 903 can be any of an RS-232 port for use with a modem based dialup connection, a copper or fiber 10/100/1000 Ethernet port, or a Bluetooth® or WiFi interface, for example. Communication port(s) 903 may be chosen depending on a network such a Local Area Network (LAN), Wide Area Network (WAN), or any network to which the computer system 900 connects. Main memory 908 can be Random Access Memory (RAM), or any other dynamic storage device(s) commonly known to one of ordinary skill in the art. Read only memory 906 can be any static storage device(s) such as Programmable Read Only Memory (PROM) chips for storing static information such as instructions for processor 902, for example.

Mass storage 907 can be used to store information and instructions. For example, flash memory or other storage media may be used, including removable or dedicated memory in a mobile or portable device, according to embodiments of the present invention. As another example, hard disks such as SCSI drives, an optical disc, an array of disks such as RAID, or any other mass storage devices may be used. Bus 901 communicably couples processor(s) 902 with the other memory, storage and communication blocks. Bus 901 can be a PCI/PCI-X or SCSI based system bus depending on the storage devices used, for example. Removable storage media 905 can be any kind of external hard-drives, floppy drives, flash drives, zip drives, compact disc-read only memory (CD-ROM), compact disc-re-writable (CD-RW), or digital video disk-read only memory (DVD-ROM), for example. The components described above are meant to exemplify some types of possibilities. In no way should the aforementioned examples limit the scope of the invention, as they are only exemplary embodiments of computer system 900 and related components.

Figure 10:
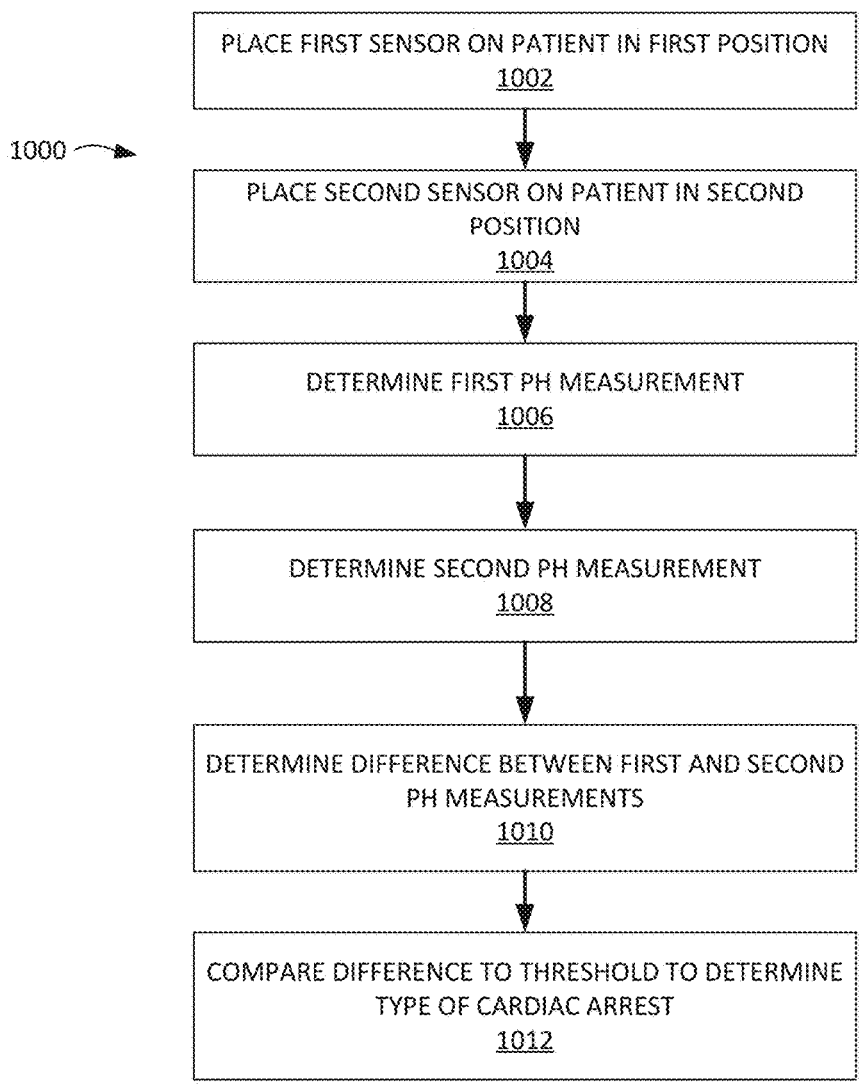
FIG. 10 is a flow chart depicting an illustrative method for determining a type of cardiac arrest affecting a patient, according to embodiments of the present invention.

FIG. 10 is a flow chart depicting an illustrative method 1000 for distinguishing between arrhythmic cardiac arrest and asphyxia cardiac arrest in a patient who is undergoing cardiac arrest. Embodiments of the method 1000 include placing a first spectral sensor on a patient's skin in a first position near the patient's core (block 1002). The first spectral sensor may include one or more radiation sources and at least one detector and may be placed over any number of different muscles near the patient's core such as, for example, a deltoid muscle, a trapezius muscle, a latissimus dorsi muscle, and/or the like. The method 1000 also includes placing a second spectral sensor on a patient's skin in a second position near the patient's periphery (block 1004). The second spectral sensor also may include one or more radiation sources and at least one detector and may be placed over any number of different muscles near the patient's periphery such as, for example, a calf muscle, a forearm muscle, and/or the like. In embodiments, the first and second spectral sensors may be, or include, near-infrared spectroscopy (NIRS) sensors.

Embodiments of the method 1000 further include determining, using the first spectral sensor, a first measurement of pH (block 1006); determining, using the second spectral sensor, a second measurement of pH (block 1008); and determining a difference between the first measurement and the second measurement (block 1010). As shown in FIG. 10, the difference is compared to a threshold to determine the type of cardiac arrest (block 1012). For example, if the difference is greater than the threshold, a processor (e.g., the processor 902 depicted in FIG. 9) may determine that the cardiac arrest is an arrhythmic arrest; and, if the difference is less than the threshold, the processor may determine that the cardiac arrest is an asphyxia arrest. In embodiments, the threshold may be determined based on experimental results, theoretical considerations, and/or the like. Additionally, as explained above, any number of additional measurements may be obtained and analyzed to determine the type of cardiac arrest that is affecting the patient such as, for example, $SmO_2$, $SpO_2$, ECG measurements, and/or the like. In some embodiments, the method 1000 may be adapted by measuring, in addition to or in place of the first and/or second pH measurements, tissue lactate and/or tissue oxygenation parameters. Just as previously described for tissue pH measurements, the difference between these other parameters can be determined (similar to block 1010) and this difference compared to a threshold to determine the type of cardiac arrest (similar to block 1012). In other embodiments, if the patient's $ETCO_2$ exceeds 35 in early stages of resuscitation, this may indicate an increased likelihood that the arrest was caused by asphyxia rather than arrhythmia. This can then be incorporated along with tissue pH and $SmO_2$ measurements in the decision logic for arrest etiology determination. Because measurements such as pH and $SmO_2$ do not require a pulse to be present for measurement, these may be used to determine a type of cardiac arrest that is affecting a patient who does not have a pulse.

In some cases, a patient's cerebral oxygenation level is expected to decrease at different rates depending on whether the patient is suffering from a cardiac arrest of arrhythmic etiology or asphyxial etiology. Cerebral oxygenation levels can be measured using, for example, spectral sensor 1200 described above in relation to FIGS. 12, 13A and 13B. FIG.

14 depicts a conceptual plot 1400 of a patient's cerebral oxygenation level 1404 (which may be measured as a percent of oxygenation) versus time 1402. In conceptual plot 1400, time axis 1402 proceeds from left to right, and time $T_0$ indicates the beginning of the patient's cardiac arrest. Plot line 1406 indicates the expected decrease in cerebral oxygenation level for an arrhythmic cardiac arrest, while plot line 1408 indicates the expected decrease in cerebral oxygenation level for an asphyxia cardiac arrest. As can be seen in plot 1400, both plot lines will eventually reach the same or similar minimum cerebral oxygenation levels over time. However, the patient's cerebral oxygenation level is expected to decrease faster over time (e.g., reach the lowest expected cerebral oxygenation value faster) for an arrhythmic cardiac arrest compared to an asphyxia cardiac arrest.

Figure 15:
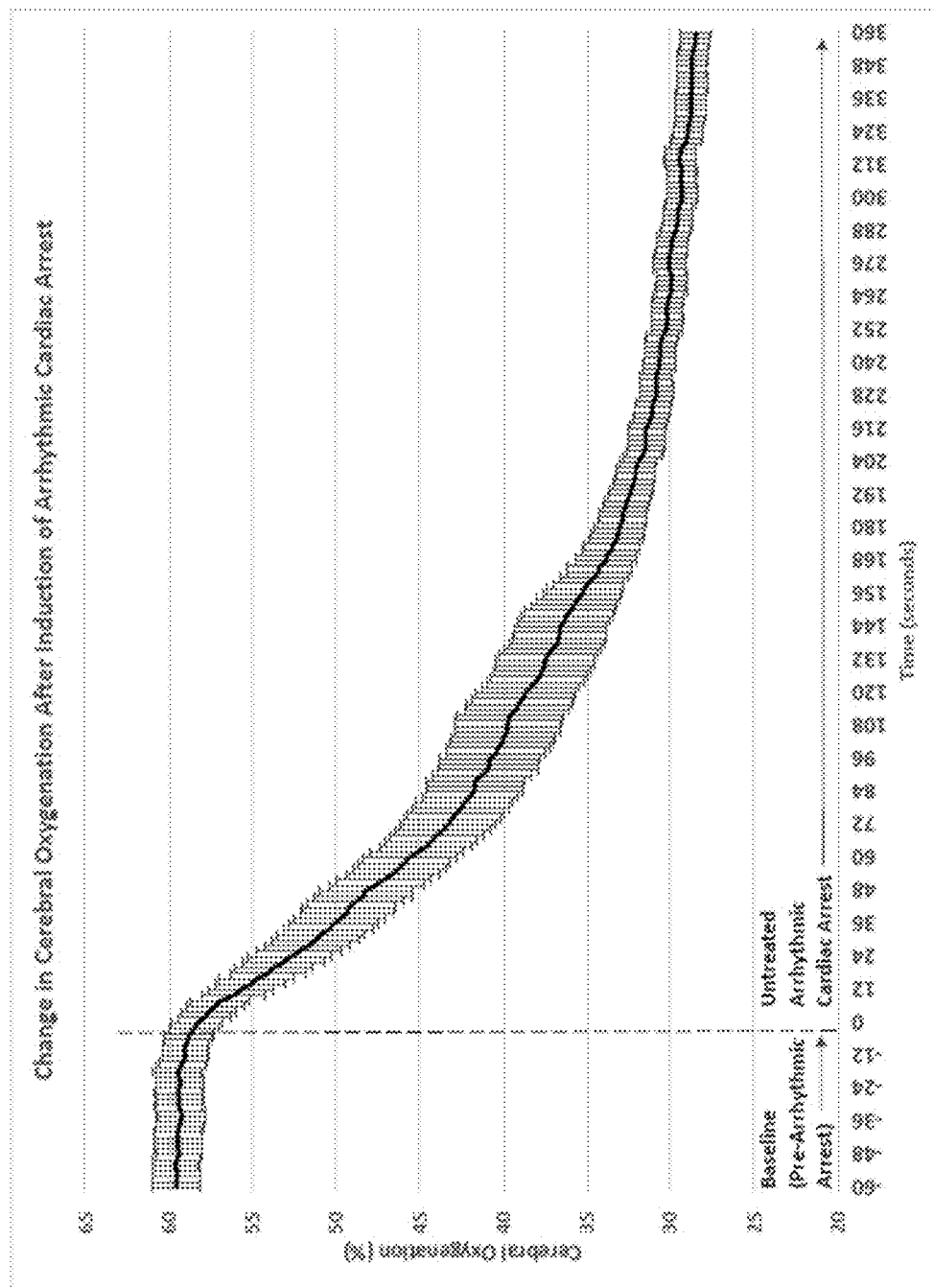
FIG. 15 depicts observed experimental data regarding changes in cerebral oxygenation measured by a cerebral spectral sensor after inducement of arrhythmic cardiac arrest in animal subjects.

FIG. 15 depicts observed experimental data regarding changes in cerebral oxygenation measured by a cerebral spectral sensor (e.g., spectral sensor 1200) after inducement of arrhythmic cardiac arrest in animal test subjects. As can be seen, the baseline cerebral oxygenation level before inducement of arrhythmic cardiac arrest is approximately 60%. The baseline cerebral oxygenation level can be less than 100% even before inducement of cardiac arrest because some cerebral spectral sensors can measure both oxygenated, arterial blood as well as de-oxygenated, venous blood. After inducement of arrhythmic cardiac arrest, cerebral oxygenation level drops rapidly—within 30 seconds, cerebral oxygenation has been observed to drop to levels between 45-50%, and within 360 seconds (or about 6 minutes), cerebral oxygenation has been observed to drop below 30%. Although not shown in FIG. 15, cerebral oxygenation levels are expected to drop less rapidly in the event of an asphyxial cardiac arrest.

Figure 16:
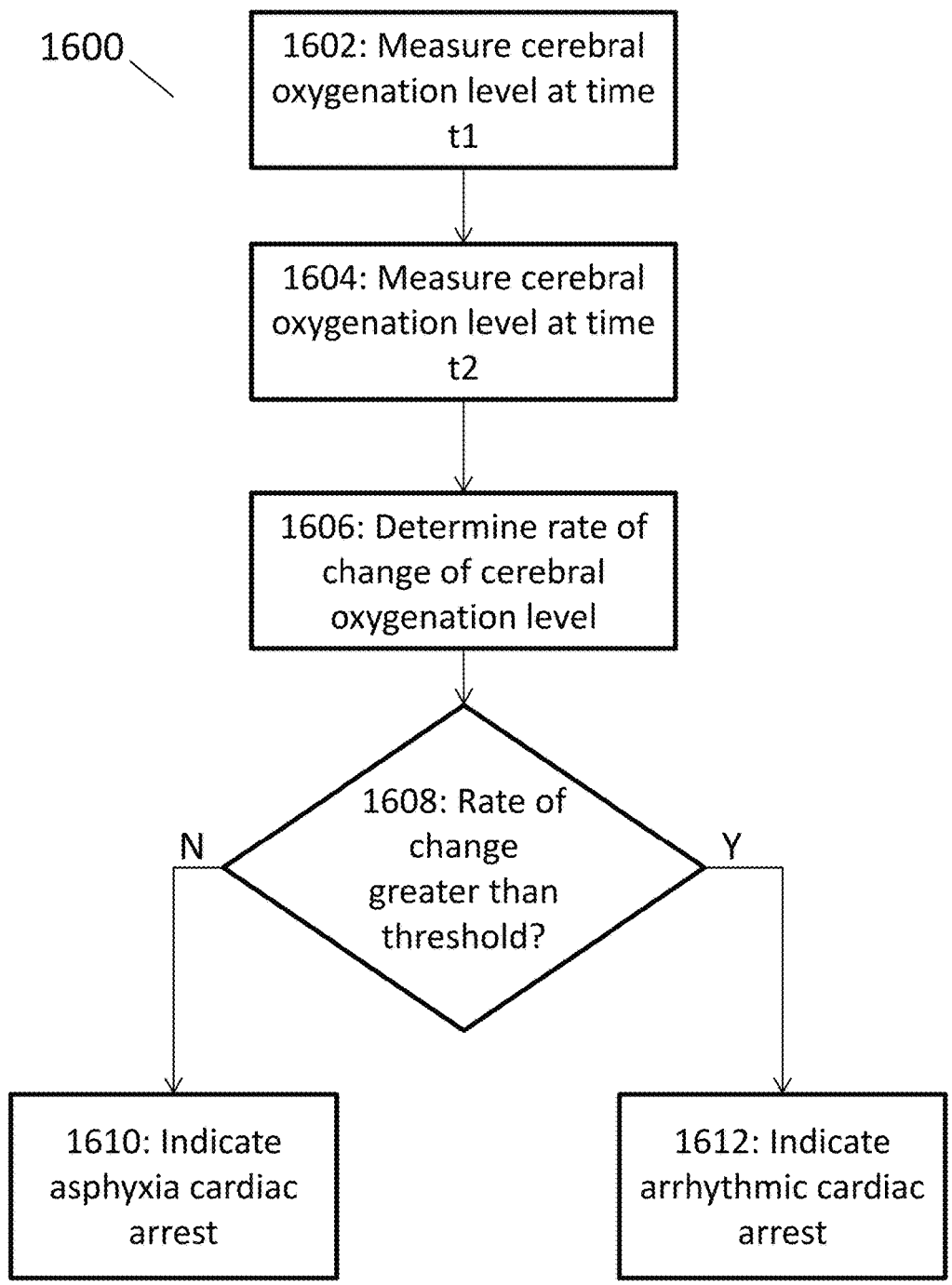
FIG. 16 is a flow chart depicting an exemplary process for distinguishing between arrhythmic cardiac arrest and asphyxia cardiac arrest by measuring a patient's cerebral oxygenation level, according to embodiments of the present invention.

Since the rate at which a patient's cerebral oxygenation level decreases can be different depending on whether the patient is suffering from an arrhythmic or asphyxial cardiac arrest, measuring the patient's cerebral oxygenation level can be used to determine the type of cardiac arrest a patient is suffering from. FIG. 16 depicts an exemplary process 1600 for distinguishing between arrhythmic cardiac arrest and asphyxia cardiac arrest in a patient who is undergoing cardiac arrest. Embodiments of the method 1600 include measuring the patient's cerebral oxygenation level at a first time t1 (block 1602). This measurement may be conducted using a cerebral spectral sensor (e.g., sensor 1200 discussed above in relation to FIGS. 12, 13A and 13B). The method 1600 also includes measuring the patient's cerebral oxygenation level at a second time t2 (block 1604). In some cases, time t2 may be after time t1. Embodiments of the method 1600 further include determining a rate of change of cerebral oxygenation level based on the measurements taken at time t1 and t2 (block 1606). This rate of change may comprise, for example, an estimated percentage drop in cerebral oxygenation level per period of time, e.g., one second, ten seconds, thirty seconds, or one minute. As shown in FIG. 16, the rate of change can be compared to a threshold to determine the type of cardiac arrest (block 1608). For example, if the rate of change is greater than the threshold, a processor (e.g., the processor 902 depicted in FIG. 9) may determine that the cardiac arrest is an arrhythmic cardiac arrest (block 1612). On the other hand, if the rate of change is less than the threshold, the processor may determine that the cardiac arrest is an asphyxia cardiac arrest (block 1610).

Figure 17:
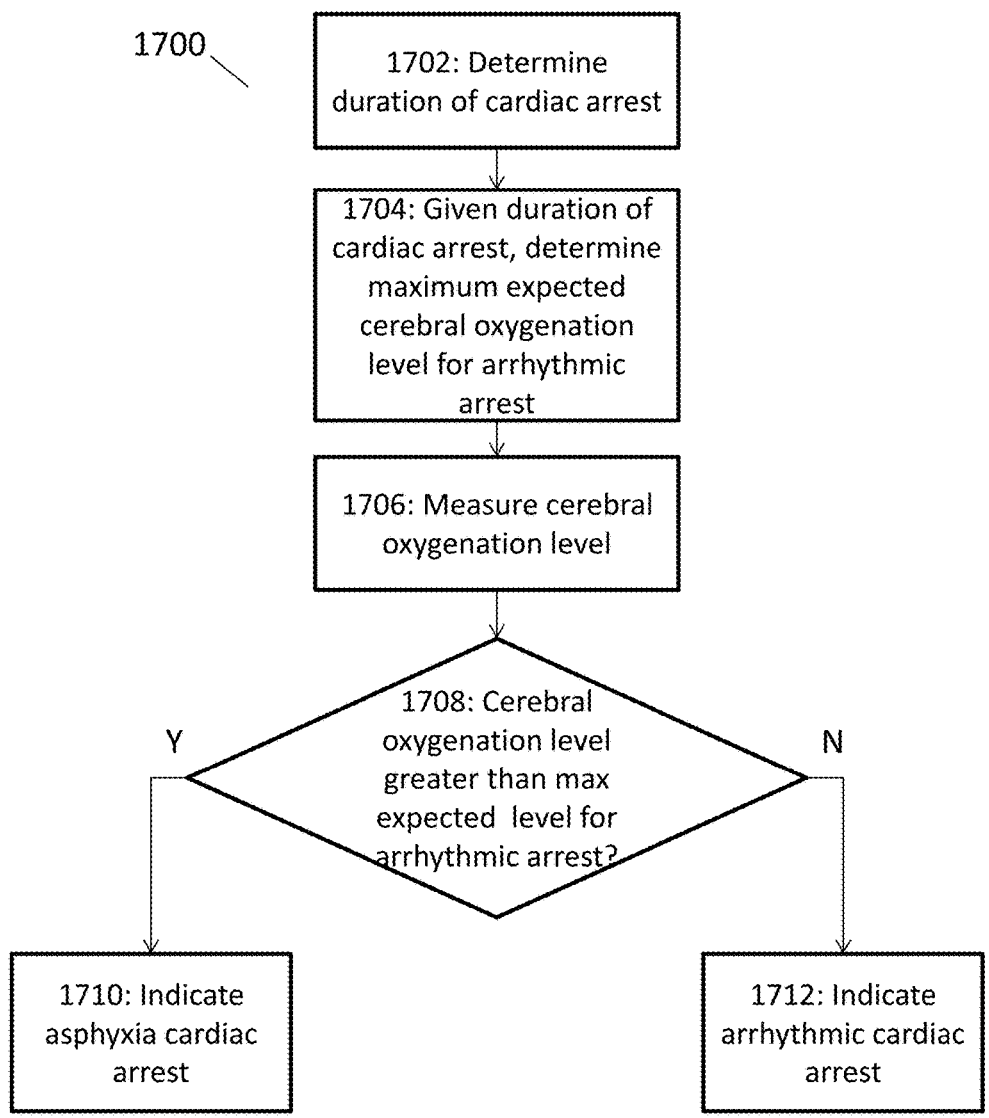
FIG. 17 is a flow chart depicting another exemplary process for distinguishing between arrhythmic cardiac arrest and asphyxia cardiac arrest by measuring a patient's cerebral oxygenation level, according to embodiments of the present invention.

FIG. 17 depicts another exemplary process 1700 for distinguishing between arrhythmic cardiac arrest and asphyxia cardiac arrest in a patient who is undergoing cardiac arrest. Embodiments of the process 1700 include determining a duration of the cardiac arrest (e.g., the patient's "downtime") (block 1702). This can be done by determining the time at which the cardiac arrest was first reported or observed, or through other means of estimating the patient's downtime. The process 1700 can further include determining the maximum expected cerebral oxygenation level for an arrhythmic cardiac arrest, given the duration of the cardiac arrest (block 1704). Since the patient's cerebral oxygenation level is expected to change with time, this determination may be based at least partly on the patient's downtime (other additional factors may also be considered). For example, the maximum expected cerebral oxygenation level can be determined using a lookup table that compares the patient's downtime with observed experimental data. As an illustrative example, the observed experimental data in FIG. 15 (or similar data) can be used to determine that the maximum expected cerebral oxygenation level for an arrhythmic arrest after 60 seconds of downtime is approximately 47%, and the maximum expected cerebral oxygenation level for an arrhythmic arrest after 180 seconds of downtime is approximately 34%. Other values for expected cerebral oxygenation levels in different circumstances are also possible. Alternatively, the maximum expected cerebral oxygenation level can be determined using a formula derived from observed experimental data that takes into account the patient's downtime. Embodiments of the process 1700 can further include measuring the patient's cerebral oxygenation level (block 1706). As shown in FIG. 17, the patient's measured cerebral oxygenation level can be compared to the maximum expected cerebral oxygenation level for an arrhythmic arrest (block 1708). If the patient's measured cerebral oxygenation level is greater than the maximum expected level for an arrhythmic arrest, a processor (e.g., the processor 902 depicted in FIG. 9) may determine that the cardiac arrest is an asphyxia cardiac arrest (block 1710). On the other hand, if the patient's measured cerebral oxygenation level is less than or equal to the maximum expected level for an arrhythmic arrest, the processor may determine that the cardiac arrest is an arrhythmic cardiac arrest (block 1712).

In some embodiments, process 1700 may also be modified to compute the minimum expected cerebral oxygenation level for an asphyxia arrest instead of the maximum expected cerebral oxygenation level for an arrhythmic arrest in block 1704. In such embodiments, if the patient's cerebral oxygenation level is less than the minimum expected cerebral oxygenation level for an asphyxia arrest, the processor may indicate an arrhythmic arrest; conversely, if the patient's cerebral oxygenation level is greater than or equal to the minimum expected cerebral oxygenation level for an asphyxia arrest, the processor may indicate an asphyxia arrest.

Although the conceptual plots, experimental data, and processes described above in relation to FIGS. 14, 15, 16, and 17 have been discussed in relation to changes in a patient's cerebral oxygenation levels, similar conceptual plots, experimental data, and processes may also be formulated that relate to a patient's measured cerebral pH level. As discussed above, spectral sensor 1200 may be configured to measure tissue (cerebral) pH level in addition to, or instead of, tissue oxygenation level. Similar to cerebral oxygenation levels, cerebral pH levels are also expected to decrease over time in the event of a cardiac arrest (e.g., cerebral tissue is expected to grow more acidic over time during a cardiac arrest). Furthermore, cerebral pH levels are expected to decrease faster in the event of an arrhythmic cardiac arrest than in the event of an asphyxia cardiac arrest. This difference in the rate at which cerebral pH levels decrease depending on the type of cardiac arrest may also be used to distinguish between an arrhythmic cardiac arrest and an asphyxia cardiac arrest. For example, the process 1600 depicted in FIG. 16 may be adapted to measure cerebral pH levels instead of cerebral oxygenation levels in block 1602 and 1604, and to determine a rate of change of cerebral pH levels instead of a rate of change of cerebral oxygenation levels in block 1606. The rate of change of cerebral pH levels can then be compared to a threshold (similar to block 1608). If the rate of change of cerebral pH level is greater than the threshold, the processor may indicate arrhythmic cardiac arrest (similar to block 1612). On the other hand, if the rate of change of cerebral pH level is less than or equal to the threshold, the processor may indicate asphyxia cardiac arrest (similar to block 1610).

The process 1700 depicted in FIG. 17 may also be adapted to use cerebral pH levels instead of cerebral oxygenation levels. For example, the process 1700 can be adapted to determine the maximum expected cerebral pH level for an arrhythmic cardiac arrest, given the duration of the cardiac arrest (similar block 1704). This determination may be done using methods similar to those described above in relation to block 1704 for FIG. 17, except applied to cerebral pH levels instead of cerebral oxygenation levels. The patient's cerebral pH level can then be measured (similar to block 1706). The patient's measured cerebral pH level can then be compared to the maximum expected cerebral pH level for an arrhythmic cardiac arrest (similar to block 1708). If the patient's cerebral pH level is greater than the maximum expected threshold, the processor can indicate asphyxia cardiac arrest (block 1710). On the other hand, if the patient's cerebral pH level is less than or equal to the maximum expected threshold, the processor can indicate an arrhythmic cardiac arrest (block 1712). Also in some embodiments, the process 1700 may be modified to compute the minimum expected cerebral pH level for an asphyxia arrest instead of the maximum expected cerebral pH level for an arrhythmic arrest in block 1704. In such embodiments, if the patient's cerebral pH level is less than the minimum expected cerebral pH level for an asphyxia arrest, the processor may indicate an arrhythmic arrest; conversely, if the patient's cerebral pH level is greater than or equal to the minimum expected cerebral pH level for an asphyxia arrest, the processor may indicate an asphyxia arrest.

Various modifications and additions can be made to the exemplary embodiments discussed without departing from the scope of the present invention. For example, the embodiments described above may further include providing a prompt to a user based on the determination of whether the patient's cardiac arrest should be treated as a cardiac arrest of arrhythmic etiology or asphyxial etiology. These prompts may be implemented through such common means as text on a display, voice or audio prompts, or pictorial diagrams displayed on a display of a measuring device or on a separate display such as an iphone or ipad or other portable computing device connected to the measuring device via such known means as Bluetooth, WiFi, etc. Also, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

The invention claimed is:

1. A system for distinguishing between arrhythmic cardiac arrest and asphyxial cardiac arrest in a patient who is undergoing cardiac arrest, the system comprising:
one or more spectral sensors, wherein the one or more spectral sensors are configured for placement above muscle tissue of the patient; and
a processor communicably coupled to the one or more spectral sensors, wherein the processor is configured to:
determine at least one of tissue pH, tissue lactate and tissue oxygenation based on input received from the one or more spectral sensors; and
determine, based on the at least one of tissue pH, tissue lactate and tissue oxygenation, whether the cardiac arrest is of arrhythmic or asphyxial etiology,
wherein at least one of the one or more spectral sensors is configured to be positioned at a core location of the patient, the core location selected to result in the at least one spectral sensor obtaining measurements from tissue perfused primarily by core blood vessels, and
wherein the processor is configured to determine an estimated time at which the patient entered cardiac arrest, wherein the determination of whether the cardiac arrest is of arrhythmic or asphyxia etiology is based at least in part on the estimated time.

2. The system of claim 1, wherein the core location corresponds to at least one of a tongue of the patient, a back of the neck of the patient, an area associated with an upper shoulder of the patient, a deltoid muscle, a latissimus dorsi muscle and the head of the patient.

3. The system of claim 1, wherein the processor is configured to:
determine a difference between the determined at least one of tissue pH, tissue lactate and tissue oxygenation and a baseline level for the at least one of tissue pH, tissue lactate and tissue oxygenation; and
the determination of whether the cardiac arrest is of arrhythmic or asphyxia etiology is based at least in part on the determined difference.

4. The system of claim 1, wherein at least one of the one or more spectral sensors is configured to be positioned at a peripheral location of the patient.

5. The system of claim 4, wherein the peripheral location comprises at least one of a forearm of the patient, a calf muscle and a forearm muscle.

6. The system of claim 1, wherein the processor is further configured to obtain an electrocardiogram (ECG) of the patient.

7. The system of claim 1, wherein at least a portion of a radiation spectrum sensed by the one or more spectral sensors and used to obtain measurements comprises one or more of a visible light region, a near-infrared light region and an ultraviolet light region.

8. The system of claim 1, wherein at least one of the one or more spectral sensors comprises a near-infrared spectroscopy (NIRS) sensor.

9. The system of claim 1, wherein the one or more spectral sensors are placed on a patient that does not have a pulse.

10. A system for distinguishing between arrhythmic cardiac arrest and asphyxial cardiac arrest in a patient who is undergoing cardiac arrest, the system comprising:
one or more spectral sensors, wherein the one or more spectral sensors are configured for placement above muscle tissue of the patient; and
a processor communicably coupled to the one or more spectral sensors, wherein the processor is configured to:

determine at least one of tissue pH, tissue lactate and tissue oxygenation based on input received from the one or more spectral sensors; and determine, based on the at least one of tissue pH, tissue lactate and tissue oxygenation, whether the cardiac arrest is of arrhythmic or asphyxial etiology, wherein at least one of the one or more spectral sensors is configured to be positioned at a core location of the patient, the core location selected to result in the at least one spectral sensor obtaining measurements from tissue perfused primarily by core blood vessels, wherein at least one of the one or more spectral sensors is configured to be positioned at a peripheral location of the patient, and wherein the processor is further configured to determine whether the cardiac arrest is of arrhythmic or asphyxial etiology based on a difference between at least one of tissue pH, tissue lactate and tissue oxygenation determined at the core location and the peripheral location.

11. The system of claim 10, wherein the processor is further configured to compare the difference to a threshold, wherein:
if the difference is greater than the threshold, the processor is configured to determine that the cardiac arrest is of arrhythmic etiology; and
if the difference is less than the threshold, the processor is configured to determine that the cardiac arrest is of asphyxial etiology.

12. The system of claim 10, wherein the processor is further configured to obtain an electrocardiogram (ECG) of the patient.

13. The system of claim 10, wherein at least a portion of a radiation spectrum sensed by the one or more spectral sensors and used to obtain measurements comprises one or more of a visible light region, a near-infrared light region and an ultraviolet light region.

14. The system of claim 10, wherein at least one of the one or more spectral sensors comprises a near-infrared spectroscopy (NIRS) sensor.

15. A system for distinguishing between arrhythmic cardiac arrest and asphyxial cardiac arrest in a patient who is undergoing cardiac arrest, the system comprising:
one or more spectral sensors, wherein the one or more spectral sensors are configured for placement above muscle tissue of the patient; and
a processor communicably coupled to the one or more spectral sensors, wherein the processor is configured to:
determine at least one of tissue pH, tissue lactate and tissue oxygenation based on input received from the one or more spectral sensors; and
determine, based on the at least one of tissue pH, tissue lactate and tissue oxygenation, whether the cardiac arrest is of arrhythmic or asphyxial etiology, wherein the processor is further configured to:
obtain a first measurement corresponding to at least one of tissue pH, tissue lactate and tissue oxygenation at a core location; and
obtain a second measurement corresponding to at least one of tissue pH, tissue lactate and tissue oxygenation at a peripheral location.

16. The system of claim 15, wherein determining whether the cardiac arrest is of arrhythmic or asphyxial etiology comprises comparing the first measurement and the second measurement.

17. The system of claim 16, wherein comparing comprises comparing the first measurement and the second measurement to a threshold.

18. The system of claim 15, wherein the processor is further configured to obtain an electrocardiogram (ECG) of the patient.

19. The system of claim 15, wherein at least a portion of a radiation spectrum sensed by the one or more spectral sensors and used to obtain measurements comprises one or more of a visible light region, a near-infrared light region and an ultraviolet light region.

20. The system of claim 15, wherein at least one of the one or more spectral sensors comprises a near-infrared spectroscopy (NIRS) sensor.

21. A system for distinguishing between arrhythmic cardiac arrest and asphyxial cardiac arrest in a patient who is undergoing cardiac arrest, the system comprising:
one or more spectral sensors, wherein the one or more spectral sensors are configured for placement above muscle tissue of the patient; and
a processor communicably coupled to the one or more spectral sensors, wherein the processor is configured to:
determine at least one of tissue pH, tissue lactate and tissue oxygenation based on input received from the one or more spectral sensors; and
determine, based on the at least one of tissue pH, tissue lactate and tissue oxygenation, whether the cardiac arrest is of arrhythmic or asphyxial etiology, wherein the processor is further configured to:
determine at least two of tissue pH, tissue lactate and tissue oxygenation based on input received from the one or more spectral sensors; and
determine whether the cardiac arrest is of arrhythmic or asphyxia etiology based on the at least two of tissue pH, tissue lactate and tissue oxygenation.

22. The system of claim 21, wherein the at least two comprise tissue pH and tissue oxygenation and the processor is further configured to:
determine that the tissue oxygenation is below a first threshold;
determine that a pH value is above a second threshold; and
determine the cardiac arrest is of arrhythmic etiology.

23. The system of claim 21, wherein the at least two comprise tissue pH and tissue oxygenation and the processor is further configured to:
determine that the tissue oxygenation is below a first threshold;
determine that a pH value is below a second threshold; and
determine the cardiac arrest is of asphyxial etiology.

24. The system of claim 23, wherein the processor is further configured to indicate early ventilation.

25. The system of claim 21, wherein the processor is further configured to obtain an electrocardiogram (ECG) of the patient.

26. The system of claim 21, wherein at least a portion of a radiation spectrum sensed by the one or more spectral sensors and used to obtain measurements comprises one or more of a visible light region, a near-infrared light region and an ultraviolet light region.

27. The system of claim 21, wherein at least one of the one or more spectral sensors comprises a near-infrared spectroscopy (NIRS) sensor.

28. A system for distinguishing between arrhythmic cardiac arrest and asphyxial cardiac arrest in a patient who is undergoing cardiac arrest, the system comprising:
one or more spectral sensors, wherein the one or more spectral sensors are configured for placement above muscle tissue of the patient; and a processor communicably coupled to the one or more spectral sensors, wherein the processor is configured to:
   determine at least one of tissue pH, tissue lactate and tissue oxygenation based on input received from the one or more spectral sensors; and
   determine, based on the at least one of tissue pH, tissue lactate and tissue oxygenation, whether the cardiac arrest is of arrhythmic or asphyxial etiology,
wherein determining at least one of tissue pH, tissue lactate and tissue oxygenation comprises:
   determining a first value corresponding to the at least one of tissue pH, tissue lactate and tissue oxygenation at a first depth; and
   determining a second value corresponding to the at least one of tissue pH, tissue lactate and tissue oxygenation at a second depth.

29. The system of claim 28, wherein the processor is further configured to obtain an electrocardiogram (ECG) of the patient.

30. The system of claim 28, wherein at least a portion of a radiation spectrum sensed by the one or more spectral sensors and used to obtain measurements comprises one or more of a visible light region, a near-infrared light region and an ultraviolet light region.

31. The system of claim 28, wherein at least one of the one or more spectral sensors comprises a near-infrared spectroscopy (NIRS) sensor.

32. A system for distinguishing between arrhythmic cardiac arrest and asphyxial cardiac arrest in a patient who is undergoing cardiac arrest, the system comprising:
   one or more spectral sensors, wherein the one or more spectral sensors are configured for placement above muscle tissue of the patient; and
   a processor communicably coupled to the one or more spectral sensors, wherein the processor is configured to:
   determine a pH value based on input received from the one or more spectral sensors; and
   determine, based on the pH value, whether the cardiac arrest is of arrhythmic or asphyxial etiology,
      wherein the one or more sensors comprises a spectral sensor configured to measure pH of the patient's muscle tissue at a plurality of depths, and the processor is further configured to:
      determine a first pH value of underlying muscle tissue; and
      determine a second pH value of underlying muscle tissue.

33. The system of claim 32, wherein the processor is further configured to determine a difference between the first pH value and the second pH value.

34. The system of claim 33, wherein the processor is further configured to compare the difference between the first pH value and the second pH value to a threshold to determine whether the cardiac arrest is of arrhythmic or asphyxial etiology.

35. The system of claim 32, wherein the first pH value is a core pH value and the second pH value is a peripheral pH value.

36. The system of claim 32, wherein the first pH value is at a first depth and the second pH value is at a second depth.

37. The system of claim 32, wherein the processor is further configured to:
   determine a physiological parameter based on input received from the one or more spectral sensors; and
   determine whether the cardiac arrest is of arrhythmic or asphyxia etiology based on the physiological parameter and the pH value.

38. The system of claim 37, wherein the physiological parameter is lactate, tissue oxygenation, or both.

39. The system of claim 32, wherein the processor is further configured to obtain an electrocardiogram (ECG) of the patient.

40. The system of claim 32, wherein at least a portion of a radiation spectrum sensed by the one or more spectral sensors and used to obtain measurements comprises one or more of a visible light region, a near-infrared light region and an ultraviolet light region.

41. The system of claim 32, wherein at least one of the one or more spectral sensors comprises a near-infrared spectroscopy (NIRS) sensor.

* * * * *